US011229489B2

(12) United States Patent
Merette et al.

(10) Patent No.: US 11,229,489 B2
(45) Date of Patent: Jan. 25, 2022

(54) SOFT TISSUE BALANCING IN ARTICULAR SURGERY

(71) Applicant: Zimmer, Inc., Warsaw, IN (US)

(72) Inventors: Jean-Sebastien Merette, Mont-St-Hiliare (CA); Harlan Levine, Tenafly, NJ (US); Pierre Couture, Montreal (CA); Olivier Boisvert, Montreal (CA); Emily Gogarty, Montreal (CA); Marc-Antoine Dufour, Warsaw, IN (US); Vincent Masse, Motreal (CA)

(73) Assignee: Zimmer, Inc., Warsaw, IN (US)

( * ) Notice: Subject to any disclaimer, the term of this patent is extended or adjusted under 35 U.S.C. 154(b) by 445 days.

(21) Appl. No.: 15/853,657

(22) Filed: Dec. 22, 2017

(65) Prior Publication Data

US 2018/0132949 A1    May 17, 2018

Related U.S. Application Data

(63) Continuation-in-part of application No. 15/624,621, filed on Jun. 15, 2017, now Pat. No. 10,136,952.
(Continued)

(51) Int. Cl.
*A61B 34/00* (2016.01)
*A61B 5/00* (2006.01)
(Continued)

(52) U.S. Cl.
CPC ............ *A61B 34/25* (2016.02); *A61B 5/1075* (2013.01); *A61B 5/4533* (2013.01);
(Continued)

(58) Field of Classification Search
CPC ....... A61B 34/25; A61B 34/10; A61B 5/1075; A61B 17/154; A61B 2034/107;
(Continued)

(56) References Cited

U.S. PATENT DOCUMENTS 5,682,886 A  11/1997 Delp et al.
6,478,753 B2  11/2002 Reay-young
(Continued)

FOREIGN PATENT DOCUMENTS

CN  101612055  12/2009
CN  105592817  5/2016
(Continued)

OTHER PUBLICATIONS

Fickert, S, et al. "Precision of Ci-Navigated Extension and Flexion Gap Balancing in Total Knee Arthroplasty and Analysis of Potential Predictive Variables." Archives of Orthopaedic and Trauma Surgery, U.S. National Library of Medicine, Nov. 2011, pubmed.ncbi.nlm.nih.gov/22072193/. Accessed Dec. 14, 2020 (Year: 2011).*
(Continued)

*Primary Examiner* — Marcela I. Shirsat
(74) *Attorney, Agent, or Firm* — Schwegman Lundberg & Woessner, P.A.

(57) ABSTRACT

Systems and methods may be used to perform robot-aided surgery. A system may include a display device and a computing device including a memory device with instructions. The instructions can cause the system to access surgical data, calculate medial and lateral gap data, calculate a recommended component set, and generate a graphical user interface. Accessing surgical data can include accessing soft tissue data indicative of at least tension in soft tissues surrounding a surgical location. The graphical user interface can include an interactive trapezoidal graphic overlaid onto a graphical representation of a distal femur and a proximal tibia. The interactive trapezoidal graphic can include a graphical representation of a medial total gap, a lateral total gap, and a recommended spacer size. The interactive trapezoidal graphic can update in response to adjustments in implant parameters to assist in surgical planning.

18 Claims, 24 Drawing Sheets

Related U.S. Application Data

(60) Provisional application No. 62/501,585, filed on May 4, 2017, provisional application No. 62/424,732, filed on Nov. 21, 2016, provisional application No. 62/375,049, filed on Aug. 15, 2016, provisional application No. 62/350,958, filed on Jun. 16, 2016.

(51) Int. Cl.

| | | |
|---|---|---|
| *A61B 34/10* | (2016.01) | |
| *G06F 3/0484* | (2013.01) | |
| *A61B 5/107* | (2006.01) | |
| *A61B 17/56* | (2006.01) | |
| *A61B 17/02* | (2006.01) | |
| *A61B 17/17* | (2006.01) | |
| *G06T 11/60* | (2006.01) | |
| *G06T 11/20* | (2006.01) | |
| *A61B 17/15* | (2006.01) | |

(52) U.S. Cl.
CPC ........ *A61B 17/025* (2013.01); *A61B 17/1764* (2013.01); *A61B 34/10* (2016.02); *G06F 3/04845* (2013.01); *G06F 3/04847* (2013.01); *G06T 11/206* (2013.01); *G06T 11/60* (2013.01); *A61B 17/154* (2013.01); *A61B 2017/0268* (2013.01); *A61B 2017/568* (2013.01); *A61B 2034/104* (2016.02); *A61B 2034/107* (2016.02); *A61B 2034/108* (2016.02); *G06T 2200/24* (2013.01); *G06T 2210/41* (2013.01)

(58) Field of Classification Search
CPC ........ A61B 2034/108; A61B 2034/104; G06F 3/04845; G06F 3/04847; G06T 2210/41
USPC ....... 606/88; 600/411, 595; 703/11; 715/705
See application file for complete search history.

(56) References Cited

U.S. PATENT DOCUMENTS

| | | |
|---|---|---|
| 7,615,055 B2 | 11/2009 | DiSilvestro |
| 8,007,448 B2 | 8/2011 | Moctesuma de La Barrera |
| 8,065,927 B2 | 11/2011 | Crottet et al. |
| 8,323,290 B2 | 12/2012 | Metzger et al. |
| 8,337,508 B2 | 12/2012 | Lavallee et al. |
| 8,394,104 B2 | 3/2013 | DiSilvestro |
| 8,556,830 B2 | 10/2013 | Sherman et al. |
| 8,571,637 B2 | 10/2013 | Sheffer et al. |
| 8,734,454 B2 | 5/2014 | DiSilvestro |
| 8,888,718 B2 | 11/2014 | Siston et al. |
| 9,259,172 B2 | 2/2016 | Stein et al. |
| 9,265,447 B2 | 2/2016 | Stein et al. |
| 9,585,615 B2 | 3/2017 | Singh et al. |
| 9,622,701 B2 | 4/2017 | Stein et al. |
| 9,636,185 B2 | 5/2017 | Quaid et al. |
| 10,206,792 B2 | 2/2019 | Sherman et al. |
| 10,729,417 B2 | 8/2020 | Cole et al. |
| 10,758,375 B2 | 9/2020 | Walker et al. |
| 10,973,659 B2 | 4/2021 | Cabot |
| 2002/0052606 A1 | 5/2002 | Bonutti |
| 2003/0069644 A1 | 4/2003 | Kovacevic et al. |
| 2003/0153978 A1 | 8/2003 | Whiteside |
| 2004/0030245 A1 | 2/2004 | Noble et al. |
| 2004/0097951 A1 | 5/2004 | Steffensmeier |
| 2004/0254771 A1 | 12/2004 | Riener et al. |
| 2006/0149277 A1 | 7/2006 | Cinquin et al. |
| 2006/0241569 A1 | 10/2006 | Disilvestro |
| 2007/0100258 A1 | 5/2007 | Shoham et al. |
| 2007/0156157 A1 | 7/2007 | Nahum et al. |
| 2007/0244488 A1 | 10/2007 | Metzger et al. |
| 2007/0270680 A1 | 11/2007 | Sheffer et al. |
| 2009/0043556 A1* | 2/2009 | Axelson .................. G06F 30/00 703/11 |
| 2010/0010506 A1 | 1/2010 | Murphy |
| 2010/0198275 A1 | 8/2010 | Chana et al. |
| 2010/0234770 A1* | 9/2010 | Colombet .............. A61B 90/36 600/595 |
| 2010/0250571 A1 | 9/2010 | Pierce et al. |
| 2011/0275957 A1 | 11/2011 | Bhandari |
| 2012/0259342 A1 | 10/2012 | Chana et al. |
| 2012/0290088 A1 | 11/2012 | Amirouche et al. |
| 2013/0023794 A1 | 1/2013 | Stein et al. |
| 2013/0066432 A1 | 3/2013 | Colwell et al. |
| 2013/0296868 A1 | 11/2013 | Bonutti |
| 2014/0188129 A1 | 7/2014 | Kang |
| 2014/0189508 A1* | 7/2014 | Granchi ................. A61B 34/10 715/705 |
| 2014/0228860 A1 | 8/2014 | Steines et al. |
| 2015/0094736 A1 | 4/2015 | Malackowski et al. |
| 2015/0105782 A1 | 4/2015 | D'lima et al. |
| 2015/0106024 A1 | 4/2015 | Lightcap et al. |
| 2015/0164609 A1 | 6/2015 | Wu |
| 2015/0265291 A1 | 9/2015 | Wilkinson |
| 2016/0045268 A1 | 2/2016 | Keppler et al. |
| 2016/0081758 A1 | 3/2016 | Bonutti |
| 2016/0095694 A1 | 4/2016 | Hauri et al. |
| 2016/0228193 A1* | 8/2016 | Moctezuma de la Barrera .......... A61B 34/20 |
| 2016/0278944 A1 | 9/2016 | D'lima et al. |
| 2017/0312099 A1 | 11/2017 | Paszicsnyek |
| 2017/0360512 A1 | 12/2017 | Couture et al. |
| 2019/0053859 A1 | 2/2019 | Couture et al. |
| 2019/0290451 A1 | 9/2019 | Trabish et al. |
| 2020/0261297 A1 | 8/2020 | Strydom et al. |
| 2020/0323540 A1 | 10/2020 | Kang et al. |
| 2021/0000612 A1 | 1/2021 | Mahfouz |
| 2021/0007809 A1 | 1/2021 | Morgan |

FOREIGN PATENT DOCUMENTS

| | | |
|---|---|---|
| CN | 109640862 | 4/2019 |
| CN | 110623732 A | 12/2019 |
| EP | 0204639 B1 | 10/1990 |
| JP | 2007152100 | 6/2007 |
| JP | 2007202950 | 8/2007 |
| JP | 2008517708 | 5/2008 |
| JP | 2010240406 | 10/2010 |
| JP | 2019521755 | 8/2019 |
| JP | 2020044443 | 3/2020 |
| WO | WO-2013020026 A1 | 2/2013 |
| WO | 2017195046 | 11/2017 |
| WO | 2017218928 | 12/2017 |

OTHER PUBLICATIONS

Smith-nephew.com. 2011. Surgical Technique for Use With the Journey™ II BCS and Journey™ II CR. [online] Available at: <https://www.smith-nephew.com/global/assets/pdf/products/surgical/navio_tka_st_manual_500081revb.pdf> [Accessed Dec. 15, 2020]). (Year: 2011).*

"Australian Application Serial No. 2019204049, First Examination Report dated Mar. 6, 2020", 6 pages.

"U.S. Appl. No. 16/166,795, Restriction Requirement dated May 5, 2020", 7 pages.

"U.S. Appl. No. 15/624,621, Examiner Interview Summary dated Dec. 18, 2017", 3 pgs.

"U.S. Appl. No. 15/624,621, Response filed Sep. 27, 2017 to Restriction Requirement dated Sep. 13, 2017", 9 pgs.

"U.S. Appl. No. 15/624,621, Restriction Requirement dated Sep. 13, 2017", 8 pgs.

"De Mayo Universal Distractor®", Innovative Medical Products, Inc., (2013), 2 pgs.

"International Application Serial No. PCT/US2017/037930, International Search Report dated Sep. 26, 2017", 5 pgs.

"International Application Serial No. PCT/US2017/037930, Written Opinion dated Sep. 26, 2017", 11 pgs.

"U.S. Appl. No. 15/624,621, Final Office Action dated Apr. 26, 2018", 14 pgs.

(56) References Cited

OTHER PUBLICATIONS

"Australian Application Serial No. 2018282467, First Examination Report dated Jan. 28, 2020", 2 pgs.

"European Application Serial No. 18215519.2, Response filed Feb. 28, 2020 to Extended European Search Report dated Jul. 30, 2019", 23 pgs.

"Japanese Application Serial No. 2018-565863, Response filed Oct. 10, 2019 to Notification of Reasons for Refusal dated Jul. 16, 2019", (W/ English Translation of Claims), 15 pgs.

"U.S. Appl. No. 16/166,795, Preliminary Amendment filed Nov. 8, 2018", 6 pgs.

"International Application Serial No. PCT US2017 037930, International Preliminary Report on Patentability dated Dec. 27, 2018", 13 pgs.

"Australian Application Serial No. 2017283630, First Examination Report dated Jan. 17, 2019", 4 pgs.

U.S. Appl. No. 15/624,621, filed Jun. 15, 2017, Soft Tissue Balancing in Articular Surgery.

"Canadian Application Serial No. 3,026,416, Examiner's Rule 30(2) Requisition dated Jan. 22, 2019", 4 pgs.

"Chinese Application Serial No. 201780037103.7, Office Action dated Jun. 27, 2019", w English translation, 8 pgs.

"European Application Serial No. 18215519.2, Extended European Search dated dated Jul. 30, 2019", 7 pgs.

"Canadian Application Serial No. 3,026,416, Response filed Jul. 22, 2019 to Examiner's Rule 30(2) Requisition dated Jan. 22, 2019", 4 pgs.

"Japanese Application Serial No. 2018-565863, Notification of Reasons for Refusal dated Jul. 16, 2019", w English Translation, 8 pgs.

"European Application Serial No. 17734204.5, Response filed Aug. 8, 2019 to Office Action dated Jan. 29, 2019", 25 pgs.

"Chinese Application Serial No. 201780037103.7, Response filed Aug. 9, 2019 to Office Action dated Jun. 27, 2019", w English claims, 6 pgs.

"U.S. Appl. No. 15/624,621, Non Final Office Action dated Oct. 20, 2017", 12 pgs.

"U.S. Appl. No. 15/624,621, Response filed Jan. 17, 2018 to Non Final Office Action dated Oct. 20, 2017", 14 pgs.

"U.S. Appl. No. 15/624,621, Response filed Jun. 25, 2018 to Final Office Action dated Apr. 26, 2018", 10 pgs.

"U.S. Appl. No. 15/624,621, Advisory Action dated Jul. 6, 2018", 3 pgs.

"U.S. Appl. No. 15/624,621, Response filed Jul. 13, 2018 to Advisory Action dated Jul. 6, 2018", 5 pgs.

"U.S. Appl. No. 15/624,621, Notice of Allowance dated Jul. 23, 2018", 5 pgs.

U.S. Appl. No. 16/166,795, filed Oct. 22, 2018, Soft Tissue Balancing in Articular Surgery.

"U.S. Appl. No. 16/166,795, Non Final Office Action dated Jul. 27, 2020", 9 pgs.

"U.S. Appl. No. 16/166,795, Response filed Jul. 2, 2020 to Restriction Requirement dated May 5, 2020", 9 pgs.

"Australian Application Serial No. 2019204049, Response filed Jul. 27, 2020 to First Examination Report dated Mar. 6, 2020", 17 pgs.

"Australian Application Serial No. 2019204049, Subsequent Examiners Report dated Aug. 24, 2020", 3 pgs.

"U.S. Appl. No. 16/166,795, Response filed Oct. 27, 2020 to Non Final Office Action dated Jul. 27, 2020", 9 pgs.

"U.S. Appl. No. 16/166,795, Final Office Action dated Nov. 9, 2020", 7 pgs.

"U.S. Appl. No. 16/166,795, Response filed Jan. 11, 2021 to Final Office Action dated Nov. 9, 2020", 10 pgs.

"U.S. Appl. No. 16/166,795, Advisory Action dated Feb. 11, 2021", 2 pgs.

"U.S. Appl. No. 16/166,795, Response filed Mar. 9, 2021 to Advisory Action dated Feb. 11, 2021", 10 pgs.

"Australian Application Serial No. 2019204049, Response filed Nov. 9, 2020 to Subsequent Examiners Report dated Aug. 24, 2020", 17 pages.

"U.S. Appl. No. 16/166,795, Corrected Notice of Allowability dated Jun. 16, 2021", 2 pgs.

"U.S. Appl. No. 16/166,795, Notice of Allowance dated Jun. 2, 2021", 6 pgs.

"Canadian Application Serial No. 3,072,502, Response filed Jul. 5, 2021 to Office Action dated Mar. 3, 2021", 15 pgs.

"Japanese Application Serial No. 2019-236315, Response filed Jun. 2, 2021 to Notification of Reasons for Refusal dated Mar. 2, 2021", (W/ English Translation), 27 pgs.

"Japanese Application Serial No. 2019-236315, Notification of Reasons for Refusal dated Mar. 2, 2021", with English translation, 9 pages.

"Canadian Application Serial No. 3,072,502, Office Action dated Mar. 3, 2021", 3 pgs.

\* cited by examiner

SOFT TISSUE BALANCING IN ARTICULAR SURGERY

CLAIM OF PRIORITY

This application is a continuation-in-part of U.S. patent application Ser. No. 15/624,621, filed Jun. 15, 2017, titled "SOFT TISSUE BALANCING IN ARTICULAR SURGERY", which claims the benefit of priority to U.S. Provisional Application Ser. No. 62/350,958, filed Jun. 16, 2016, titled "METHOD AND SYSTEM FOR BALANCING SOFT TISSUE IN ARTICULAR SURGERY"; U.S. Provisional Application Ser. No. 62/375,049, filed Aug. 15, 2016, titled "METHOD AND SYSTEM FOR BALANCING SOFT TISSUE IN ARTICULAR SURGERY"; U.S. Provisional Application Ser. No. 62/424,732, filed Nov. 21, 2016, titled "SOFT TISSUE BALANCING IN ARTICULAR SURGERY"; and U.S. Provisional Application Ser. No. 62/501,585, filed May 4, 2017, titled "SOFT TISSUE BALANCING IN ARTICULAR SURGERY." The contents of the above applications are incorporated herein by reference in their entireties.

TECHNICAL FIELD

The present application relates to computer-assisted orthopedic surgery used to assist in the placement of implants at articular surfaces of bones.

BACKGROUND

Computer-assisted surgery has been developed in order to help a surgeon in altering bones, and in positioning and orienting implants to a desired location. Computer-assisted surgery may encompass a wide range of devices, including surgical navigation, pre-operative planning, and various robotic devices. One area where computer-assisted surgery has potential is in orthopedic joint repair or replacement surgeries. For example, soft tissue balancing is an important factor in articular repair, as an unbalance may result in joint instability. However, when performing orthopedic surgery on joints, soft tissue evaluations are conventionally done by hand, with the surgeon qualitatively assessing the limits of patient's range of motion. The conventional technique may result in errors or lack precision.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
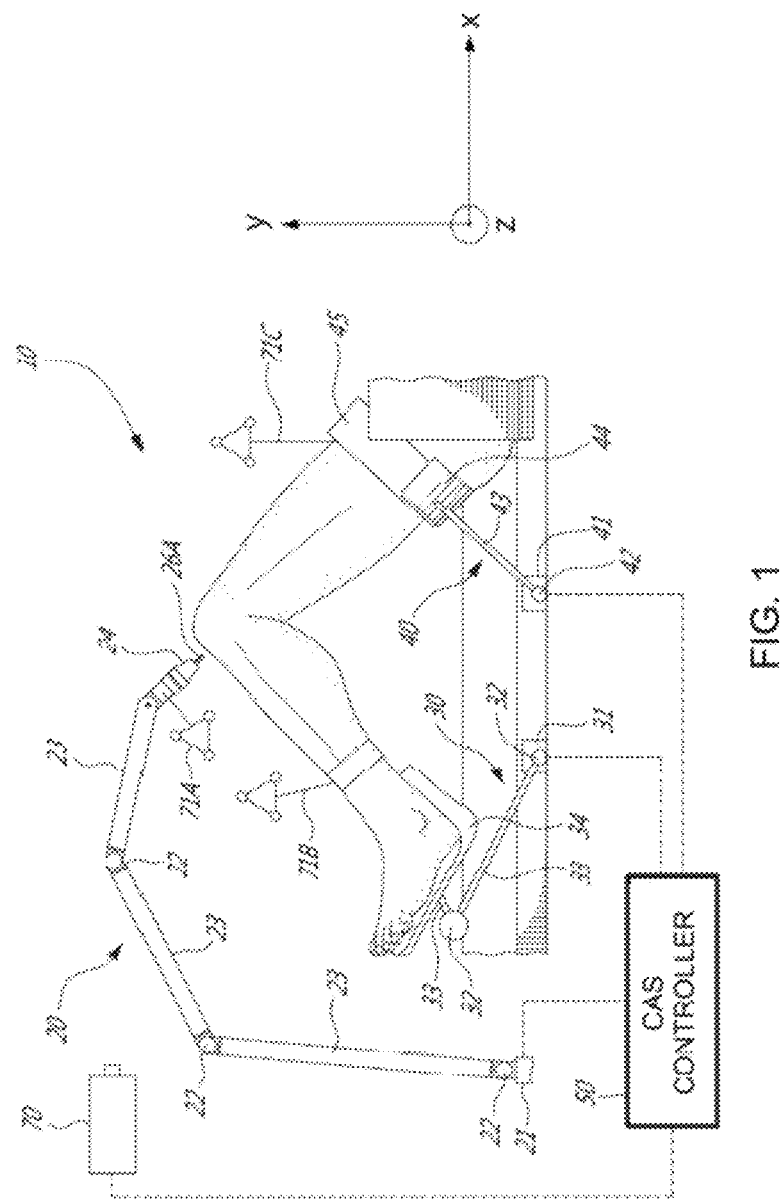
FIG. 1 is a schematic view of a CAS system in accordance with some embodiments.

The systems and methods described herein may be used for soft tissue balancing using a robotic arm. A robotic arm, used during a surgical procedure may perform a soft tissue balancing assessment. For example, a component (such as a pin, a cutting block, etc., as further described below) may anchor to a bone and the robotic arm may be driven to pull on the bone or other anatomy to perform the soft tissue balancing assessment. In an example, the soft tissue may be placed under tension to determine balance. Applied tension may be determined using information received from a force/torque sensor in the robotic arm. The robotic arm may include a sensor (e.g., inertial, optical, encoder, etc.) to measure a rotation indicative of a rotation required for soft tissue balancing. The soft tissue balancing may be performed with the robotic arm with a leg in flexion or in extension. In an example, a computer-assisted surgery (CAS) system may be used to implement or control the robotic arm. In certain examples, the computer-assisted surgery (CAS) system can generate a graphical user interface designed specifically to convey soft-tissue balancing information quickly and accurately to a surgeon while the surgeon is performing a joint arthroplasty procedure.

In an example, a robotic arm may raise an end effector (e.g., located at a distal end of the robotic arm) to displace a femur, while the tibia remains still by gravity, by its fixation to the table (e.g., when a foot support is used), by a human (e.g., surgical assistant or the surgeon), by surgical tape, self-adherent wrap or tape, or other fixing devices or components to secure the tibia. In another example, the robotic arm may use a laminar spreader to spread the bones apart. The laminar spreader may be inserted in the gap between the femoral condyles and the tibial plateau. In order to assist the laminar spreader, additional devices may be used and manipulated by the robotic arm. For example, the robotic arm may manipulate a clamp to benefit from the leveraging of the clamp to apply a greater moment of force at the bones. The laminar spreader may include a gear mechanism (e.g., planetary gear device, rack and pinion, etc.) to assist in amplifying the force of the robotic arm.

A joint laxity may be determined using a sensor on the robotic arm or a component attached to the robotic arm, such as to assist in the soft-tissue balancing at different times during a surgical procedure. For example, soft-tissue balancing may be determined prior to having the robotic arm perform an alteration to the bone, to confirm a predetermined implant size or location on the bone, or to enable adjustments to the predetermined implant size or location on the bone. In another example, the soft-tissue balancing may be determined after one or more planar resections have been made, such as to determine whether further adjustments are necessary to any of the resections.

In some examples, the computing systems supporting robotic or non-robotic joint arthroplasty can include graphical user interfaces (GUI) designed specifically to convey soft-tissue balancing information to a surgeon intraoperatively. The GUIs utilize soft-tissue balance information obtained using the robotic systems discussed herein, but can also be useful in non-robotic surgical contexts where manual devices with sensors or comparable devices are utilized to measure soft tissue tensions during a joint arthroplasty procedure.

Referring to the drawings and more particularly to FIG. 1, a computer-assisted surgery (CAS) system is generally shown at 10, and is used to perform orthopedic surgery maneuvers on a patient, including pre-operative analysis of range of motion and implant assessment planning, as described hereinafter. The system 10 is shown relative to a patient's knee joint in supine decubitus, but only as an example. The system 10 could be used for other body parts, including non-exhaustively hip joint, spine, and shoulder bones. A particular function of the CAS system 10 is assistance in planning soft tissue balancing, whereby the CAS system 10 may be used in total knee replacement surgery, to balance tension/stress in knee joint ligaments. In certain examples, discuss in greater detail below, the CAS system 10 is utilized to collect soft-tissue tension data through controlled manipulation of the target joint with measurements collected using sensors embedded in various parts of the system.

The CAS system 10 may be robotized, in which case it may have a robot arm 20, a foot support 30, a thigh support 40 and a CAS controller 50. The robot arm 20 is the working end of the system 10, and is used to perform bone alterations as planned by an operator or the CAS controller 50 and as controlled by the CAS controller 50. The foot support 30 supports the foot and lower leg of the patient, in such a way that it is only selectively movable. The foot support 30 may be robotized in that its movements may be controlled by the CAS controller 50. The thigh support 40 supports the thigh and upper leg of the patient, again in such a way that it is only selectively or optionally movable. The thigh support 40 may optionally be robotized in that its movements may be controlled by the CAS controller 50. The CAS controller 50 controls the robot arm 20, the foot support 30, or the thigh support 40. Moreover, as described hereinafter, the CAS controller 50 may perform a range-of-motion (ROM) analysis and implant assessment in pre-operative planning, with or without the assistance of an operator. The CAS controller 50 may also guide an operator through the surgical procedure, by providing intraoperative data of position and orientation and joint laxity boundaries, as explained hereinafter. The tracking apparatus 70 may be used to track the bones of the patient, and the robot arm 20 when present. For example, the tracking apparatus 70 may assist in performing the calibration of the patient bone with respect to the robot arm, for subsequent navigation in the X, Y, Z coordinate system.

Referring to FIG. 1, a schematic example of the robot arm 20 is provided. The robot arm 20 may stand from a base 21, for instance in a fixed relation relative to the operating-room (OR) table supporting the patient. In one example configuration, the OR table may consist of a 'U'-shaped end portion with each side of the 'U' supporting a leg of the patient and an open floor space existing between each leg. In this configuration, the base is positioned in the open floor space between the legs, therefore allowing the robot arm to access each leg of the patient without repositioning the base as would be desired in a bilateral total knee replacement procedure. The relative positioning of the robot arm 20 relative to the patient is a determinative factor in the precision of the surgical procedure, whereby the foot support 30 and thigh support 40 may assist in keeping the operated limb fixed in the illustrated X, Y, Z coordinate system. The robot arm 20 has a plurality of joints 22 and links 23, of any appropriate form, to support a tool head 24 that interfaces with the patient. The arm 20 is shown being a serial mechanism, arranged for the tool head 24 to be displaceable in a desired number of degrees of freedom (DOF). For example, the robot arm 20 controls 6-DOF movements of the tool head 24, i.e., X, Y, Z in the coordinate system, and pitch, roll and yaw. Fewer or additional DOFs may be present. For simplicity, only a generic illustration of the joints 22 and links 23 is provided, but more joints of different types may be present to move the tool head 24 in the manner described above. The joints 22 are powered for the robot arm 20 to move as controlled by the controller 50 in the six DOFs. Therefore, the powering of the joints 22 is such that the tool head 24 of the robot arm 20 may execute precise movements, such as moving along a single direction in one translation DOF, or being restricted to moving along a plane, among possibilities. Such robot arms 20 are known, for instance as described in U.S. patent application Ser. No. 11/610,728, incorporated herein by reference.

Referring to FIG. 1, the thigh support 40 may be robotized, static or adjustable passively. In the latter case, the thigh support 40 may be displaceable relative to the OR table, in order to be better positioned as a function of the patient's location on the table. Accordingly, the thigh support 40 is shown as including a passive mechanism, with various lockable joints to lock the thigh support 40 in a desired position and orientation. The mechanism of the thigh support 40 may have a slider 41, moving along the OR table in the X-axis direction. Joints 42 and links 43 may also be part of the mechanism of the thigh support 40, to support a thigh bracket 44. A strap 45 may immobilize the thigh/femur in the thigh support 40. The thigh support 40 may not be necessary in some instances. However, in the embodiment in which the range of motion is analyzed, the fixation of the femur via the thigh support 40 may assist in isolating joint movements.

Figure 2:
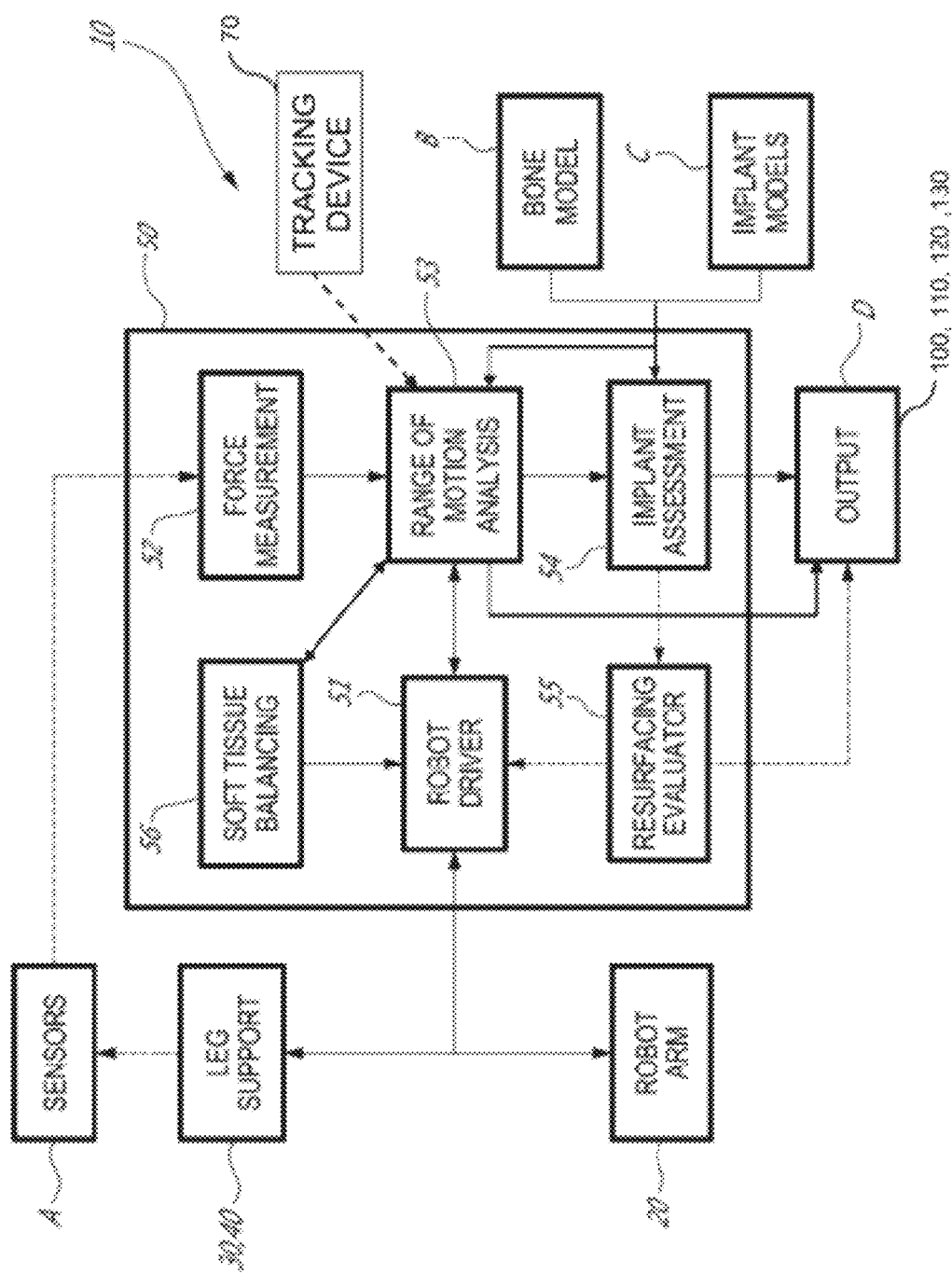
FIG. 2 is a block diagram of a CAS controller used with a robotized surgery system in accordance with some embodiments.

Referring to FIG. 2, the CAS controller 50 is shown in greater detail relative to the other components of the robotized surgery system 10. The controller 50 has a processor unit to control movement of the robot arm 20, and of the leg support (foot support 30 and thigh support 40), when applicable. The robotized surgery controller 50 provides computer-assisted surgery guidance to an operator, whether in the form of a range-of-motion (ROM) analysis or implant assessment in pre-operatively planning or during the surgical procedure. The system 10 may comprise various types of interfaces, for the information to be provided to the operator. The interfaces may be monitors or screens including wireless portable devices (e.g., phones, tablets), audio guidance, LED displays, among many other possibilities. For example, there is illustrated in FIGS. 8A-8F, 9A-9B, 10A-10D and 11A-11E graphic user interfaces (GUI) e.g., 120, 130, 220, 330, and 400 that may be operated by the system 10. The controller 50 may then drive the robot arm 20 in performing the surgical procedure based on the planning achieved pre-operatively. The controller 50 may do an intra-operative soft-tissue balancing assessment, and hence enable corrective plan cuts to be made, or guide the selection of implants or other intra-operative adjustments to the plan. The controller 50 may also perform a post-operative ROM analysis.

The controller 50 may hence have a robot driver 51, such as when the robot arm 20 is part of the CAS system 10. The robot driver 51 is tasked with powering or controlling the various joints of the robot arm 20, foot support 30 and thigh support 40, when applicable. The system may include some force feedback provided by the robot arm 20 and leg support 30,40 to avoid overextending the leg or damaging the soft tissue, and to assist in determining joint laxity boundaries. The robot driver 51 may control the foot support 30 in performing particular motions, to replicate a flexion/extension of the knee, with lateral movements, to measure soft tissue tension and analyze the range of motion of the leg, including varus/valgus. As such, the robot driver 51 may output the instant angle of flexion using the position or orientation data it uses to drive the movement of the foot support 30. Sensors A are provided on the foot support 30 or in the robot arm 20 in order to measure throughout the movement the forces indicative of the tension/stress in the joint. The sensors A must therefore be sensitive enough to detect soft tissue tension/stress through the movement of the foot support 30. In the case of the robot arm 20, the sensors A may be force-torque sensors integrated therein.

The CAS controller 50 may use a processor to implement force measurement 52. Force measurement 52 may include receiving the signals from the sensors A, and calculating the instant forces in the foot support 30, representative of the tension/stress in the knee joint, or in the robot arm 20, as exemplified hereinafter. The instant forces may be used to perform ROM analysis 53 using the processor, along with the foot support tracking data from the robot driver 51. Alternatively or additionally, the ROM analysis 53 may use tracking data received from the tracking device 70 to determine the range of motion of the leg, as explained hereinafter. The ROM analysis 53 may convert the signals from the tracking device 70 into position or orientation data. In the latter case, various types of tracking technology may be used to determine the instant flexion/extension and varus/valgus, such as optical tracking as illustrated in FIG. 1, inertial sensors, etc. With the combined data from the force measurement 52 and from the robot driver 51 or other source such as surgeon or medical professional assessment, the ROM analysis 53 may be performed. Exemplary formats of the ROM analysis 53 are shown in FIGS. 5A-7B and in FIGS. 8A-8F, described hereinafter. The information of the ROM analysis 53 may therefore be a pre-operative indication of the current varus/valgus as a function of flexion/extension. The ROM analysis 53 may be performed intra-operatively, or post-operatively, to assist in quantifying the soft tissue balancing during or resulting from surgery.

The processor may be used to perform an implant assessment 54 to determine how an implant or implants will impact the range of motion. Using the ROM analysis 53, the implant assessment 54 takes into consideration the geometrical configuration of the implants based on selectable locations on the bone. For example, the implant assessment 54 may include the bone models B from pre-operative imaging (e.g., MRI, CT-scans, 2D X-ray to 3D), whether in 3D or in multiple 2D views. The implant assessment 54 may include the implant models C, such the 3D model files including implants of different dimensions.

Figure 9A:
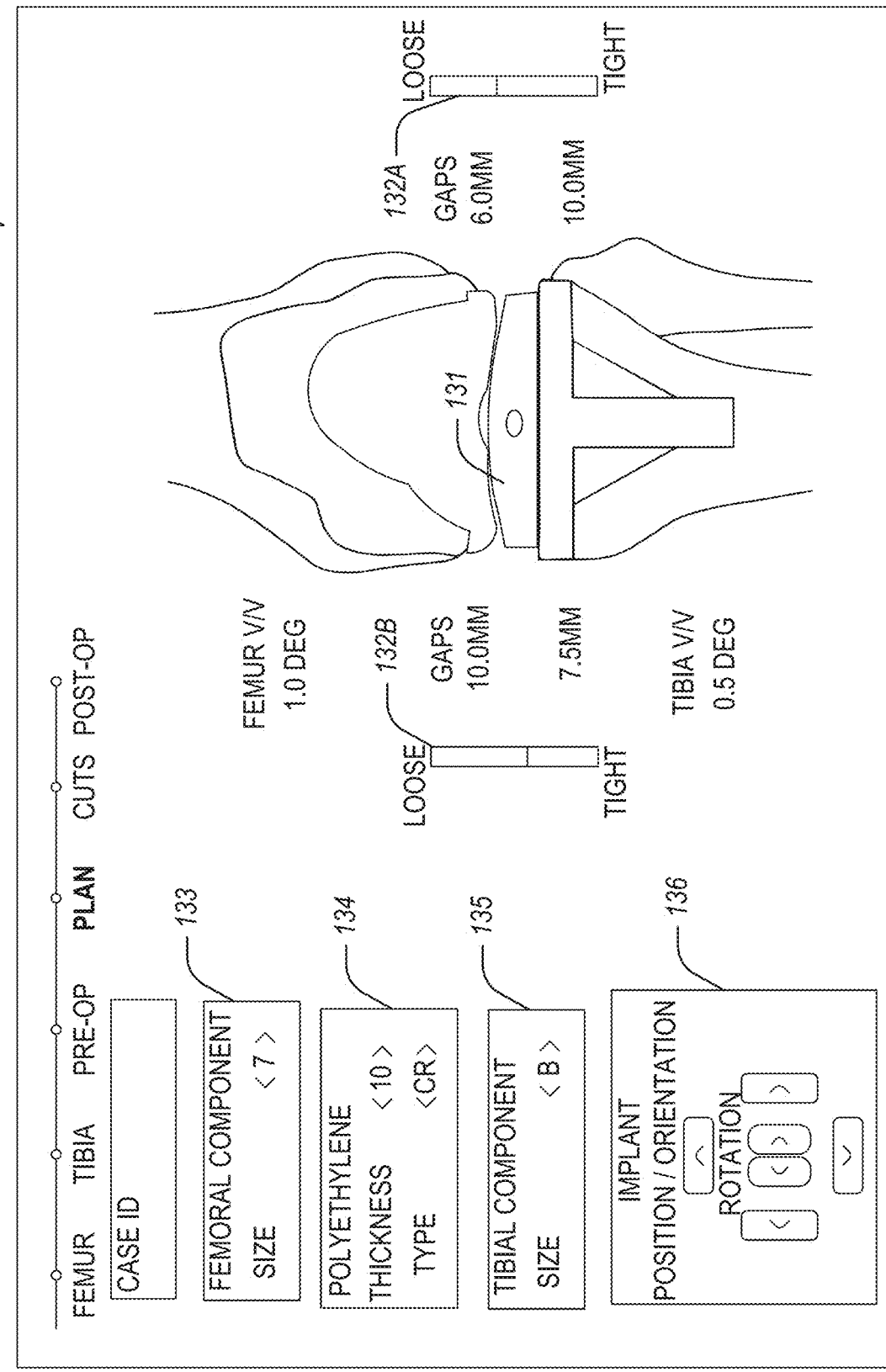
FIGS. 9A-9B are example graphic-user interfaces (GUI) for planning implant selection and locating, and for assessing resection intraoperatively or post-operatively in accordance with some embodiments.
Figure 9B:
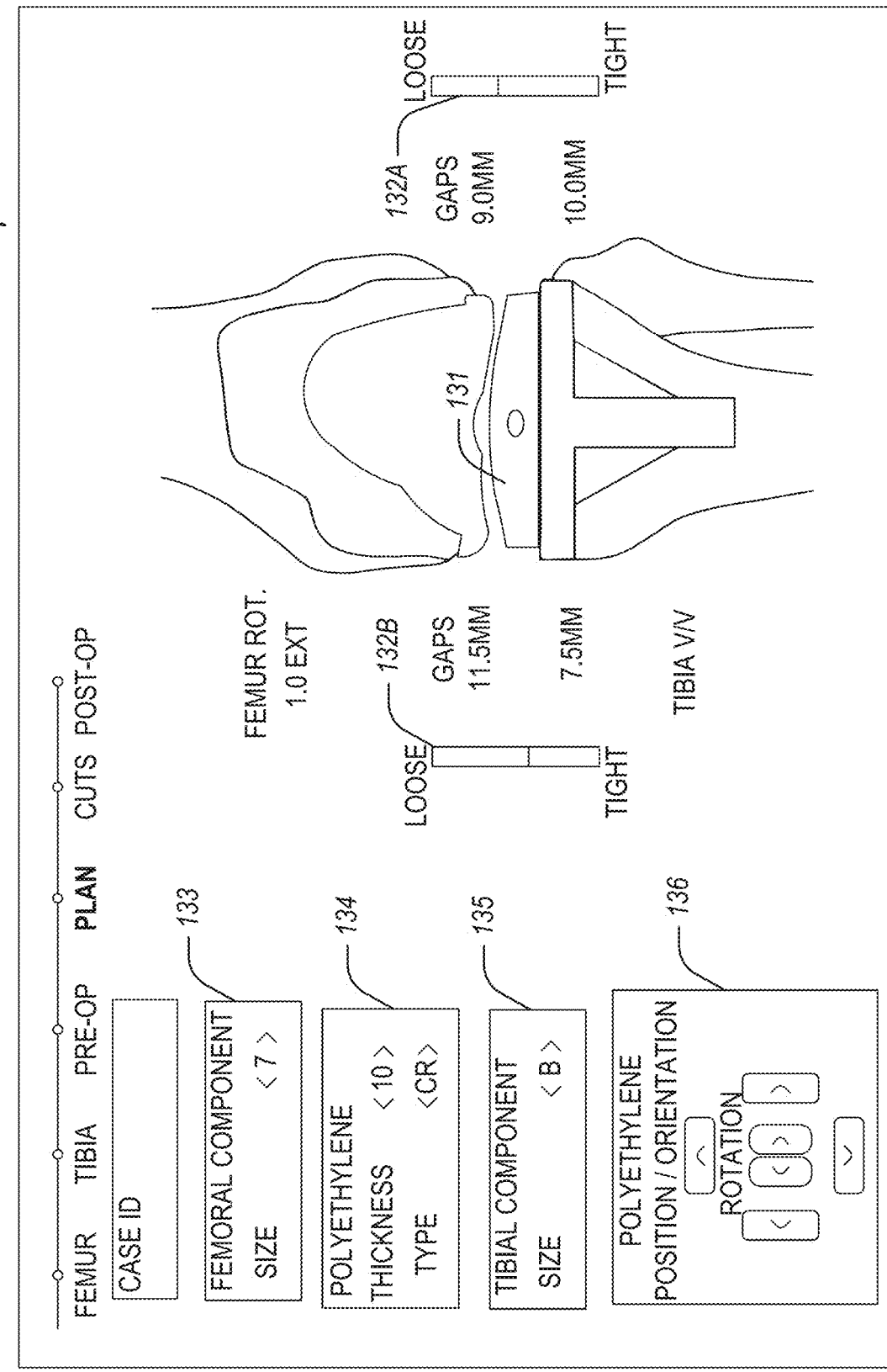

The implant assessment 54 may be performed in a fully automated manner by the processor, in evaluating from the bone model, implant models or from the ROM analysis 53 desired implant sizes and location on the bone (i.e., in position and orientation), to balance soft tissue tension/stress. Exemplary formats of the implant assessment are shown in FIGS. 9A and 9B for example, described hereinafter. The information of the implant assessment may therefore be a pre-operative or intraoperative indication of an anticipated post-surgical varus/valgus as a function of flexion/extension.

The implant assessment 54 may optionally include operator participation. The illustrations of FIGS. 9A and 9B may be GUI items, such as in GUI 130, that may be adjusted virtually manually by an operator, for the operator to see the impact on the graphs of FIGS. 6B and 7B, respectively. In such an embodiment, the implant assessment 54 may provide the assessment to assist the operator in making a decision, as opposed to automatically proposing the desired implant sizes and location on the bone. The proposal of desired implant sizes and location on the bone may be a starting point of operator navigation or decision making. When the implant sizes and location on the bone is selected or set, the implant assessment 54 may produce the output D in any appropriate format, such as GUIs 130. The format may also be that of FIGS. 11A and 11B, providing an assessment of the proposed implant sizes and location. The output D may also include bone alteration data to assist the operator or the robot arm 20 in performing the bone alterations. In such a case, the processor may perform a resurfacing evaluation 55 to calculate the bone cut volume and location, for the bone cuts that will be made based on the implant sizes and location on the bone.

The implant assessment 54 may also generate and respond to the GUI items illustrated in GUI 400 illustrated in FIGS. 11A-11E. GUI 400 provides an operator, such as a surgeon or surgical assistant, with the ability to adjust implant position, orientation, and size as well as parameters associated with the spacer size selection. The GUI 400 is designed to provide quick assessment of soft-tissue balance based on selected implant parameters. Further aspects of how the implant assessment 54 operates with respect to examples GUI 400 are discuss below in reference to FIGS. 11A-12.

The use of the tracking apparatus 70 may be determinative on the information that will be in the navigation file C, and may provide tracking data to perform the ROM analysis 53. For example, the tracking apparatus 70 may assist in performing the calibration of the patient bone with respect to the robot arm 20, for subsequent navigation in the X, Y, Z coordinate system. According to an embodiment, the tracking apparatus 70 comprises a camera that optically sees and recognizes retro-reflective references 71A, 71B, and 71B, so as to track the limbs in six DOFs, namely in position and orientation. In an embodiment featuring the robot arm 20, the reference 71A is on the tool head 24 of the robot arm 20 such that its tracking allows the controller 50 to calculate the position or orientation of the tool head 24 and tool 26A thereon. Likewise, references 71B and 71C are fixed to the patient bones, such as the tibia for reference 71B and the femur for reference 71C. As shown, the references 71 attached to the patient need not be invasively anchored to the bone, as straps or like attachment means may provide sufficient grasping to prevent movement between the references 71 and the bones, in spite of being attached to soft tissue. However, the references 71B and 71C could also be secured directly to the bones. Therefore, the ROM analysis 53 of the controller 50 may be continuously updated to obtain a current position or orientation of the robot arm 20 or patient bones in the X, Y. Z coordinate system using the data from the tracking apparatus 70. As an alternative to optical tracking, the tracking system 70 may consist of inertial sensors (e.g., accelerometers, gyroscopes, etc.) that produce tracking data to be used by the controller 50 to continuously update the position or orientation of the robot arm 20. Other types of tracking technology may also be used.

The calibration may be achieved in the manner described above, with the robot arm 20 using a registration pointer on the robot arm 20, and with the assistance of the tracking apparatus 70 when present in the robotized surgery system 10. Another calibration approach is to perform radiography of the bones with the references 71 thereon, at the start of the surgical procedure. For example, a C-arm may be used for providing suitable radiographic images. The images are then used for the surface matching with the bone model B of the patient. Because of the presence of the references 71 as fixed to the bones, the intraoperative registration may then not be necessary, as the tracking apparatus 70 tracks the position or orientation of the bones in the X, Y, Z coordinate system after the surface matching between X-ray and bone model is completed.

The robotic arm 20 may apply force to a soft tissue balancing component using an end effector component or a detachable pin guide component locked to the end effector component. The soft tissue balancing component (e.g., as described in further detail below, for example in the discussion of FIGS. 3, 4, and 10A-10D) may apply force in turn to a bone or implant component to test or configure soft tissue balance. More generally, the soft tissue balancing component may be used to perform a ligament balance pull test. Based on the pull test, a femoral rotation may be determined. The femoral rotation may be presented (e.g., using a graphical user interface, such as those described below in the discussion of FIGS. 8A-11E). In an example, the femoral implant rotation may be used to calculate a target femoral implant rotation. The target femoral implant rotation may be displayed (e.g., using a user interface, such as those described below in the discussion of FIGS. 10A-11E, for example). The target femoral implant rotation may be an inverse or opposite of the rotation of the femur rotation. For example, when the femur rotation is 3 degrees internally, the target femoral implant rotation may be 3 degrees external from the femur. The target femoral implant rotation may be further adjusted as well.

The femoral implant rotation may be determined such that the rotation may compensate for an imbalance in soft tissue tension between medial and lateral compartments. The rotation of the femur during the pull test may be directly related to the determined femoral implant rotation such that a rectangular or balanced gap results from applying the rotation. For example, when the rotation is applied to placement of the implant, the gap may be balanced between the medial and the lateral compartments. In an example, the robotic arm 502 may apply a force to perform the pull test by using the soft tissue balancing component to pull on the femur. To perform the test, the robotic arm 20 may apply one or more known loads to increase the accuracy of the determined rotation.

In an example, a torque or force sensor may be used to measure torque of one or more of the components, such as the robotic arm 20, the tool head 24, or on a component such as a soft tissue balancing component. In an example, a sensor may be used to detect ligament stress or ligament tension. In another example, a position or orientation sensor (e.g., a navigation sensor, such as a sensor located on a portion of the robotic arm 20) may be used to determine a varus or valgus angle of a target leg. The varus or valgus angle may be used to determine ligament pulling in the target leg. From the varus or valgus angle or the stress or tension on the ligament, pulling on the soft tissue may be determined and a rotation to correct the pulling may be determined, and may be output on a graphical user interface (GUI), such as that described with respect to FIGS. 10A-11E.

In an example, a ligament test or other soft tissue balancing test may be performed before a bone resection cut is performed. For example, the soft tissue balancing test may be performed before any resection of a femur or a tibia. In an example, the soft tissue balancing test may be performed after resection and implantation of an implant to verify that the soft tissue is correctly balanced. For example, a first test may be performed pre-resection, which may result in a rotation angle to be used for balancing, and a second test may be performed after the implant is inserted to verify that the rotation angle was correct or that the implant was properly seated.

Figure 3:
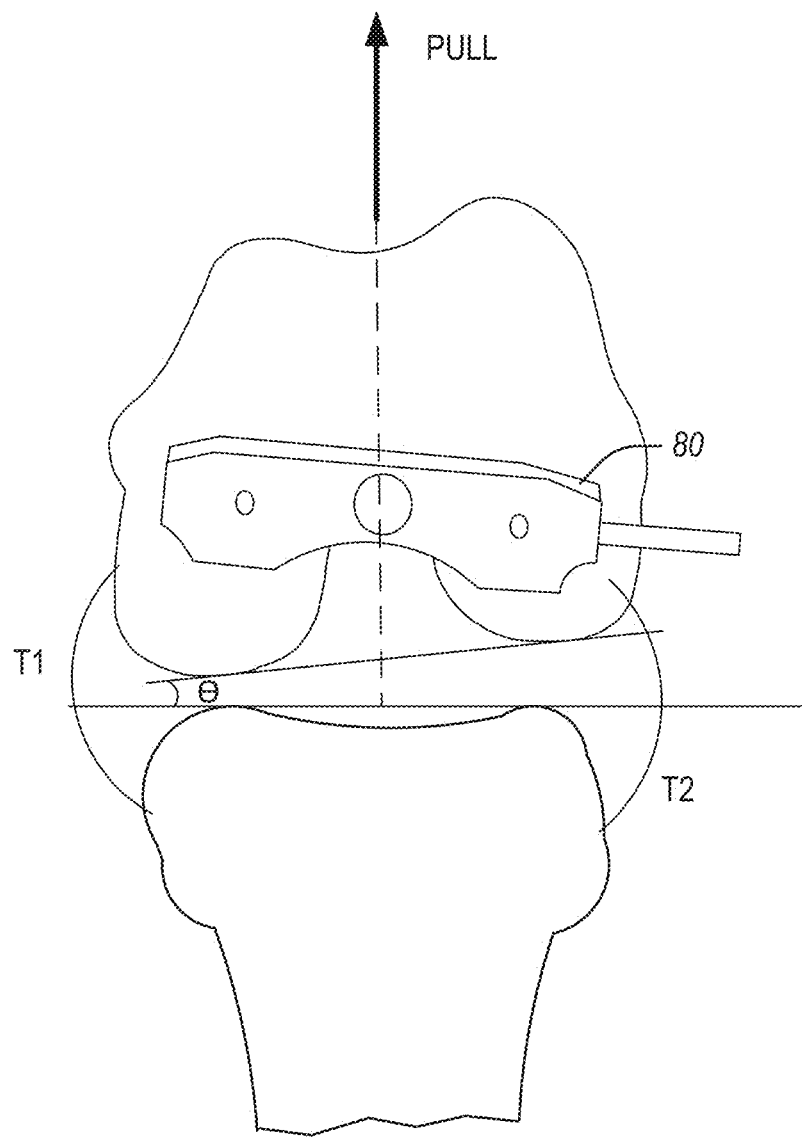
FIG. 3 is a schematic view illustrating an intraoperative soft tissue assessment using a CAS system in knee flexion in accordance with some embodiments.
Figure 4:
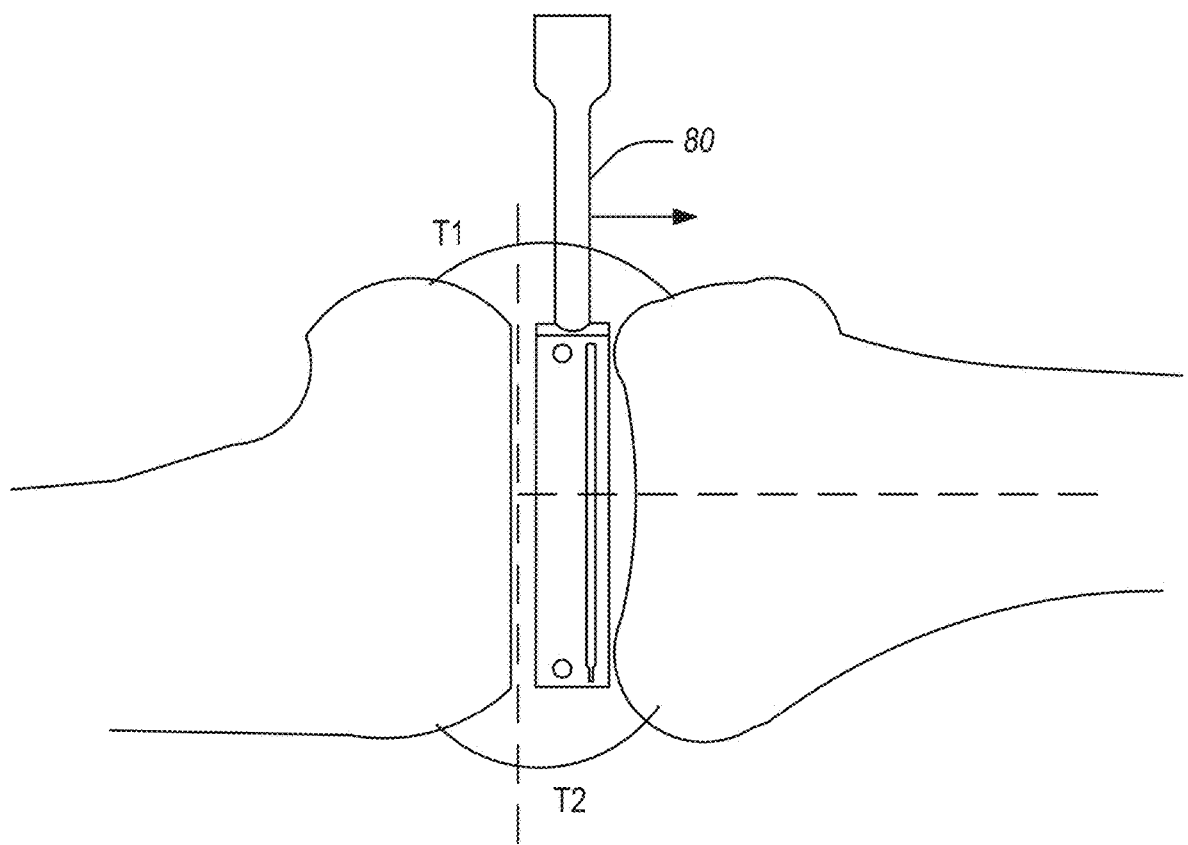
FIG. 4 is a schematic view illustrating an intraoperative soft tissue assessment using a CAS system in knee extension in accordance with some embodiments.

In an embodiment, the CAS controller 50 may operate the robot arm 20 to perform a robotized soft-tissue balancing assessment, such as by using a processor to perform soft-tissue balancing 56, although it may also be done without robotized assistance. Referring to FIG. 3, with a device 80 anchored to the bone (such as a pin, a cutting block, etc.), the robot arm 20 may be driven to pull on the bone and hence put the soft tissue under tension. Applied tension may be controlled using the signals from the force-torque sensors A in the robot arm 20 with the output of the force measurement 52. In an embodiment, the device 80 includes a pin and a cutting block. The robot arm 20 may pull the femur away from the tibia by manipulating the pin of the device 80, such that the pin (and femur) may rotate relative to the robot arm 20. The rotation of the femur will naturally go toward soft tissue balancing, in which tension T1 is equal to tension T2. The device 80 may further include an inertial sensor to measure a rotation $\theta$ indicative of the rotation required for soft tissue balancing. The rotation $\theta$ may also be monitored and measured by the robot arm 20, with appropriate sensors (optical, encoders, inertial, etc.). Referring to FIG. 4, similar operations may be performed with the leg being in extension. FIG. 4 is a schematic view illustrating an intraoperative soft tissue assessment using a CAS system in knee extension in accordance with some embodiments. In an example, the robot arm 20 may pull the femur away from the tibia, either in extension or in flexion, and automatically stop. The robot arm 20 may stop for example at a predetermined distance (gap), when a threshold force or tension is reached, or at a user-selected stopping position. The predetermined distance (e.g., 5 mm, 10 mm, a distance corresponding to a tibia implant thickness such as 10 mm, 11 mm, 12 mm, etc.), may include a safety factor (e.g., +/−1-5 mm), or the like. In an example, a combination of end position markers may be used, such as a predetermined distance approximately equal to a tibia implant thickness (e.g., an insert (poly) or the implant assembly, which may be predetermined using planning techniques), while retaining a maximum force as safety factor. For example, when a maximum force is reached before the predetermined distance, the robotic arm may be stopped. In another example, balanced ligaments may be used to mark the end position.

In FIG. 3, the soft tissue is put under tension using a robot arm, such as the robot arm 20 (not shown), acting on the device 80. In an embodiment, the robot arm 20 raises the device 80 to displace the femur, while the tibia remains still by gravity or by its fixation to the table (e.g., when a foot support 30 is used), by a human (e.g., surgical assistant or the surgeon), by surgical tape, self-adherent wrap or tape, or other fixing devices or components to secure the tibia. It is also considered to use laminar spreaders on the robot arm 20 to spread the bones apart. The laminar spreaders may be inserted in the gap between the femoral condyles and the tibial plateau. In order to assist the laminar spreaders, additional devices may be used and manipulated by the robot arm. For example, the spreaders may manipulate a clamp to benefit from the leveraging of the clamp to apply a greater moment at the bones. Likewise, the spreaders may manipulate a spreader with gear mechanism (planetary gear device, rack and pinion, etc.), to assist in amplifying the force of the robot arm.

The processor may perform soft-tissue balancing 56 to quantify joint laxity to assist in the soft-tissue balancing at different moments during the surgical procedures operated by the CAS controller 50. For example, the soft-tissue balancing 56 may assess soft-tissue balancing prior to having the robot arm 20 perform the alterations to the bone, to confirm the desired implant sizes and location on the bone produced by the implant assessment 54, or to enable adjustments to the desired implant sizes and location on the bone, and impact the output of the resurfacing evaluator 55. The soft-tissue balancing 56 may assess soft-tissue after cut planes have been made, to determine whether further adjustments are necessary.

In another embodiment, the output D is in the form of a patient-specific cut guide 3D file, for a patient-specific cut guide to be machined or 3D printed for operative use. For example, the patient-specific cut guide may have negative surfaces of the bone model for unique positioning on the bone, such that cut planes and drill guides are placed as planned. As another example, the output D may be a navigation file, of the type programmed into inertial sensor units manually navigated by an operator. Referring to FIG. 4, similar operations may be performed with the leg being in extension.

In an example, the soft tissue assessment may be performed with the leg in flexion (e.g., as shown in FIG. 3) or in extension (e.g., as shown in FIG. 4). When in flexion, the leg may be held at a 90 degree angle of flexion, or substantially 90 degrees, such as within plus or minus ten degrees. In another example, with the leg in extension, the leg may be held at zero degree angle of extension, 10 degrees, 20 degrees, or the like, such as based on surgeon preference. The soft tissue assessment may be used to measure or display gap measurements for soft tissue balancing during a test when a knee is in flexion or extension. In an example, the soft tissue balancing assessment when the knee is in flexion may include not releasing the femur when pulling. In another example, the test may include pulling on the femur, then measuring an amount of rotation that results in balance between the soft tissue (e.g., ligaments). The femur may be free to rotate to find the balance based on the amount of force on the ligaments. In an example, the soft tissue balancing assessment may be performed with the patella in place or dislocated. Additional examples of robotic soft-tissue balancing are discussed in detail within application Ser. No. 15/624,621.

Figure 5B:
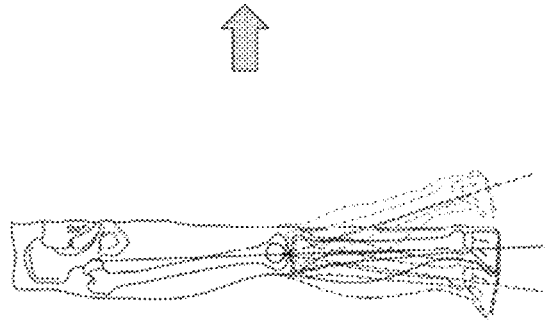
FIGS. 5A and 5B are user interfaces for displaying a range-of-motion (ROM) analysis of a CAS controller in accordance with some embodiments.
Figure 5A:
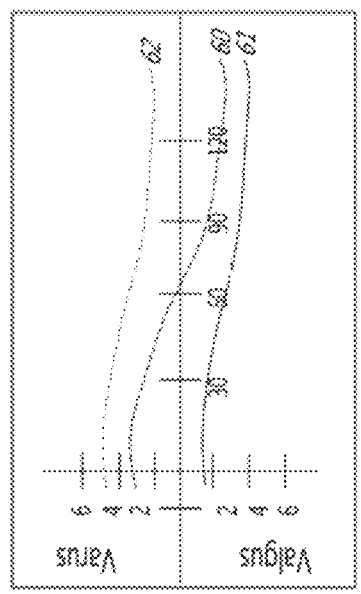
Figure 6B:
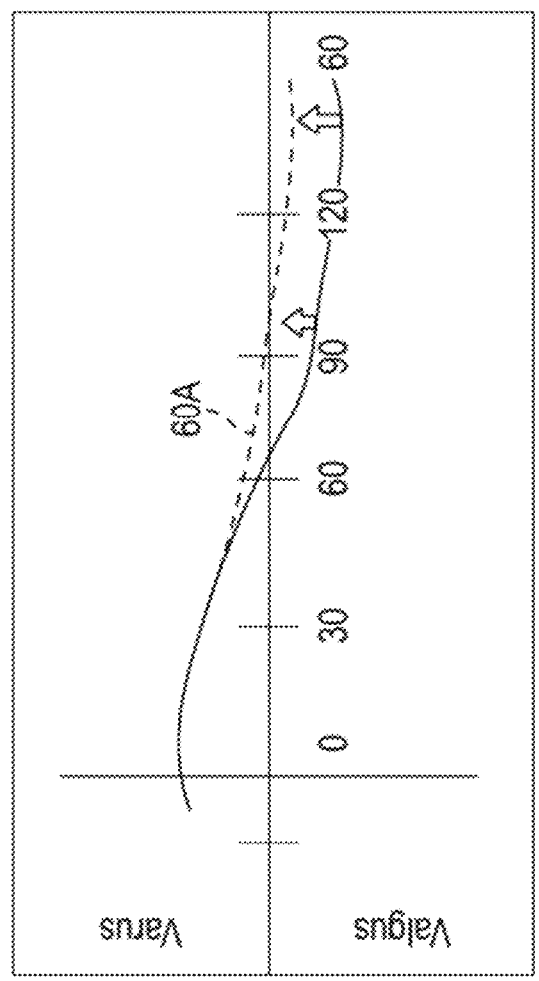
FIGS. 6A and 6B are user interfaces for displaying an implant assessment of a CAS controller, enabling implant movement from a caudal viewpoint in accordance with some embodiments.
Figure 6A:
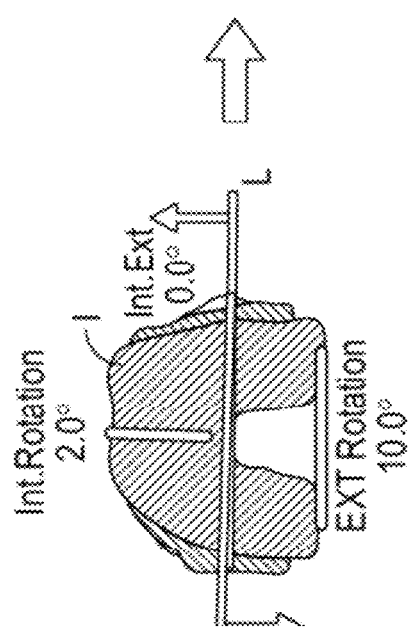
Figure 7B:
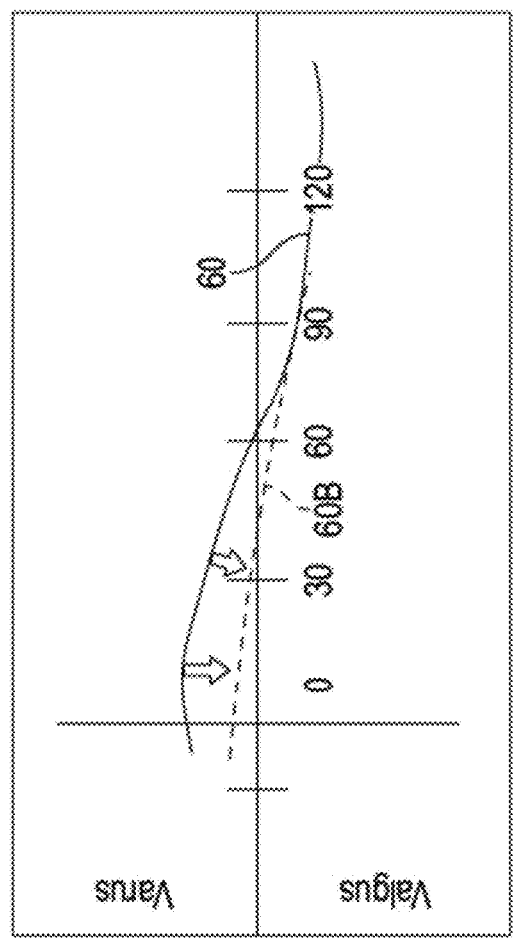
FIGS. 7A and 7B are user interfaces for displaying an implant assessment of a robotized surgery controller, enabling implant movement from a frontal viewpoint in accordance with some embodiments.
Figure 7A:
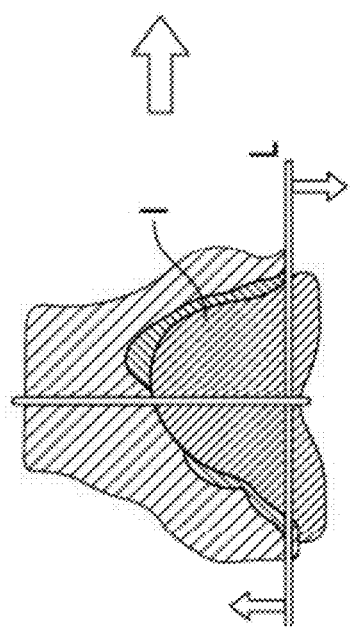

FIGS. 5A and 5B are user interfaces for displaying a range-of-motion (ROM) analysis of a CAS controller in accordance with some embodiments. FIGS. 6A and 6B are user interfaces for displaying an implant assessment of a CAS controller, enabling implant movement from a caudal viewpoint in accordance with some embodiments. FIGS. 7A and 7B are user interfaces for displaying an implant assessment of a robotized surgery controller, enabling implant movement from a frontal viewpoint in accordance with some embodiments.

Referring to FIG. 5B, a graph illustrating an actual varus/valgus balanced line 60 as a function of the leg extension is shown, as a result of the controlled movements of the foot support 30. The force measurement data allows the positioning of 60, as an indication of the varus/valgus value at balanced soft tissue. Lines 61 and 62 respectively show the valgus and varus values at maximum allowable soft tissue tension, as a result of the lateral movements depicted in FIG. 5A, as measured by the force measurement 52. The graph of FIG. 5B is the ROM analysis, done preoperatively or post-operatively.

A similar graph may be produced by the implant assessment 54, to illustrate the impact of given implants at a given location on the bones. However, as shown in FIGS. 6A and 7A, the model of the implant 1 may be rotated by an operator, with angle values being instantly updated. As a result of such virtual adjustments, the varus/valgus balanced line 60 may shift to reduce the valgus as in 60A (FIG. 6B) or to reduce the varus as in 60B (FIG. 7B). An operator or a processor performing the implant assessment 54 may therefore perform such adjustment in order to bring the balanced line 60 closer to a neutral varus/valgus through as much of the leg extension as possible.

Referring now to FIGS. 8A-8F, 9A-9B, 10A-10D, and 11A-11E, a surgical workflow that may be operated with the CAS system 10 is described, with reference to the illustrated GUIs. The expression GUI is used in the plural to indicate a variation of GUI pages in the surgical workflow. The surgical workflow may be the output D produced by the processor of the CAS controller 50. The descriptions of the following GUI may omit certain operations necessary to perform any particular arthroplasty, and are intended solely to highlight techniques used in certain aspects of certain surgical procedures.

Referring to FIGS. 8A-8F, GUI 120 is used to guide the gathering of range-of-motion data of the tracked limbs, tracked in a virtual coordinate system by a tracking system, such as tracking device 70. In an embodiment, the GUI 120 guides a human operator, such as a surgeon or medical professional, in determining the limits of the range of motion and of joint laxity, based on force felt by the operator, as an alternative to using the force feedback capability of the robotized version of the system 10. According to FIG. 8A, a lateral leg display 121 may be provided to visually illustrate the limits of flexion and extension, with related angle. The operator manually displaces the tibia relative to the femur between maximum (flexion) and minimum (extension) angles, and the tracking of the tibia and femur by the tracking device 10 allows the processor to record these angles for use in the ROM analysis 53. The operator may assist in determining the maximum and minimum angle, by judging when to stop the extension and flexion based on the resistance felt. The leg display 121 may present the measured data in different forms, using for instance a movement arch 121A to visually show the range of movement. A ROM bar 121B may also be provided, showing the numerical values of angle, including a median angle. When the extension angle value is outside of standards, the ROM analysis 53 may identify potential flexion contracture to influence the resection planning to remedy this issue. When the overall range of motion is below acceptable standards, the ROM analysis 53 may identify this condition to influence resection planning and implant selection.

Figure 8A:
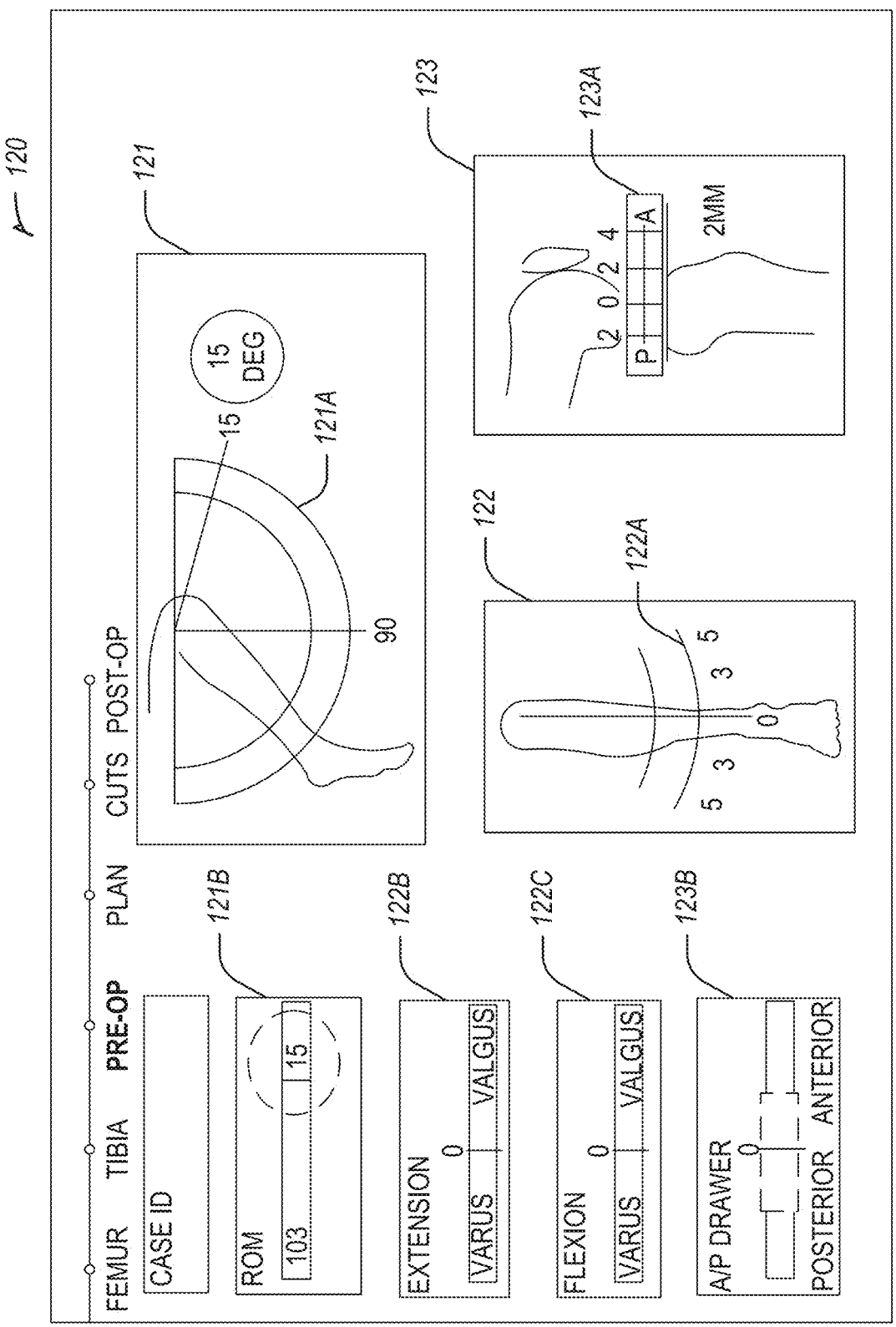
FIGS. 8A-8F are example graphic-user interfaces (GUI) guiding a quantification of joint movement for a CAS system and displaying varus and valgus angles of a knee in accordance with some embodiments.
Figure 8B:
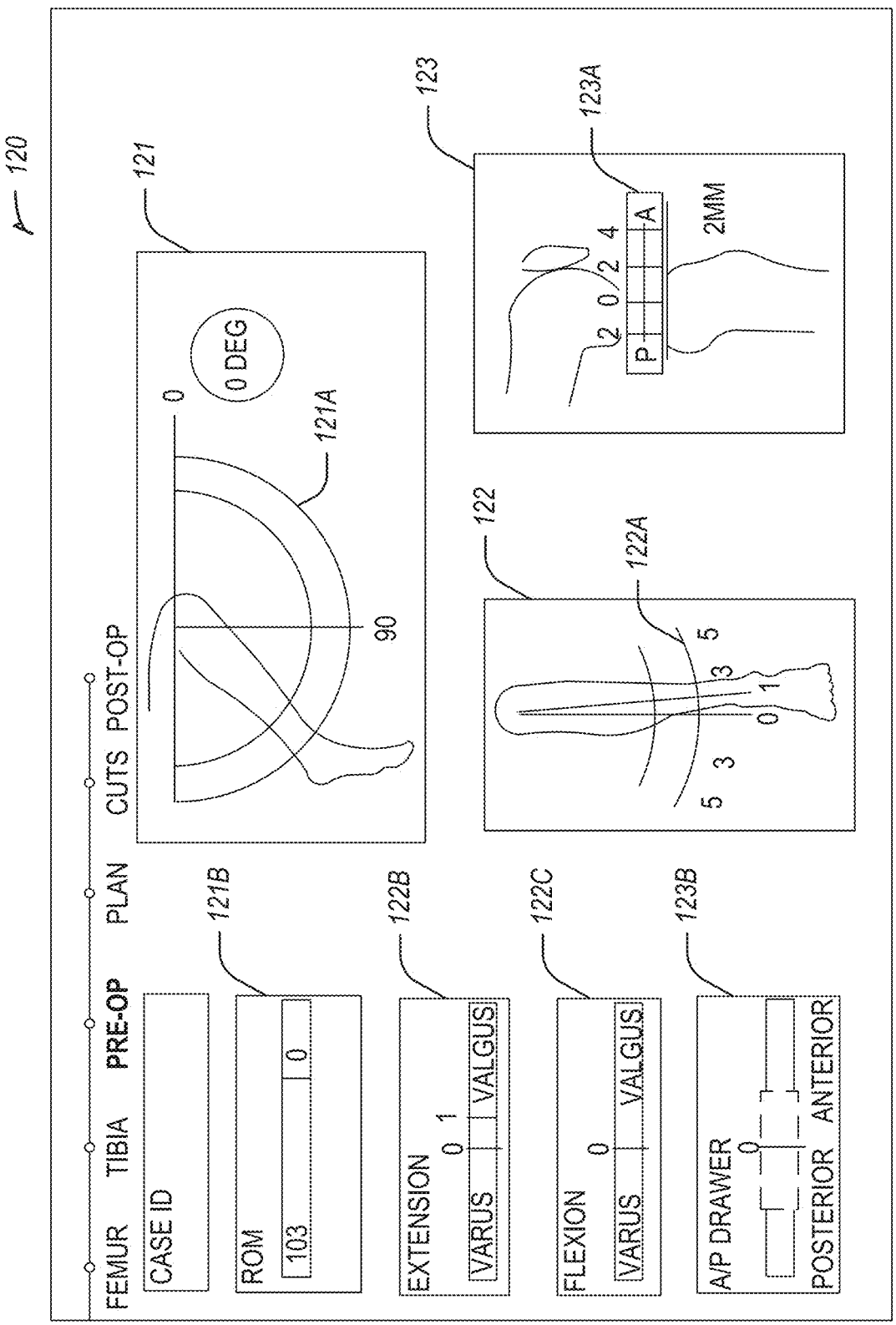

According to FIG. 8B, a frontal leg display 122 may also be provided in GUI 120 to visually illustrate the varus/valgus angles at extension and flexion. In a first step, the operator manually extends the leg, to then pivot the tibia relative to the femur to maximum varus and valgus angles, and the tracking of the tibia and femur by the tracking device 70 allows the ROM analysis 53 to use these angles. The maximum varus/valgus angles may be determined by the operator's judgement as to when to stop the extension and flexion based on the resistance felt. The frontal leg display 122 may provide the data in different forms, using also for example a movement arch 122A to visually show the range of movement, and an extension varus/valgus bar 122B, showing the numerical values of varus and valgus.

Figure 8C:
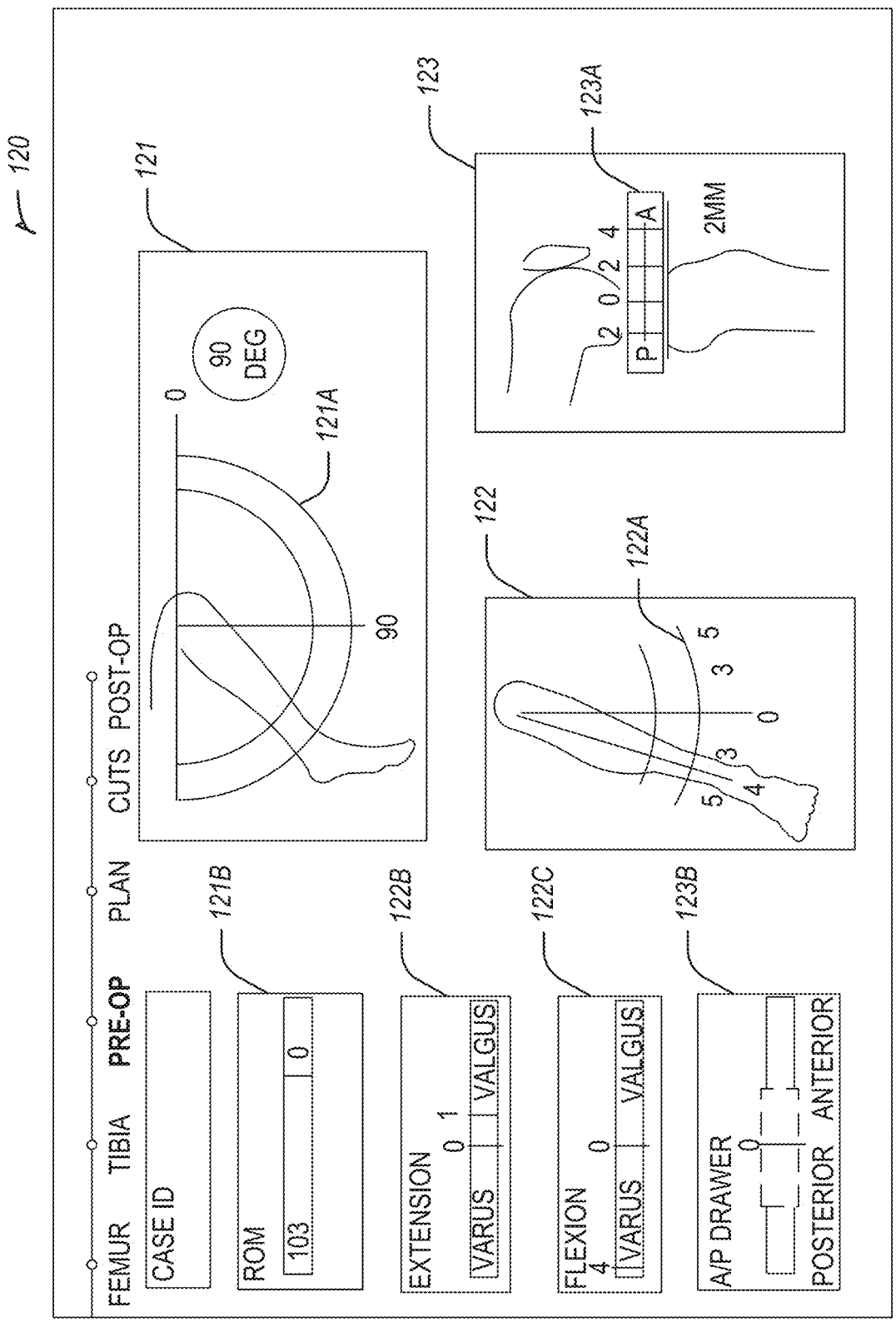

Then, according to FIG. 8C and using the same or another fontal leg display 122 and movement arch 122A, the operator manually flexes the leg, to then pivot the tibia relative to the femur to maximum varus and valgus angles, and the tracking of the tibia and femur allows the ROM analysis 53 to use these angles. A flexion varus/valgus bar 122C may then show the numerical values of varus and valgus. These values are recorded for subsequent use by the processor in performing the soft tissue balancing 56. Moreover, these values may indicate a loose or tight knee condition, laterally or medially, whether it be correctable by implant positioning or not. In the latter case, the system 10 may suggest ligament releasing to remedy the condition. The soft tissue balancing 56 may identify such a condition by being programmed with acceptable varus/valgus angle ranges. The varus/valgus angles obtained may be representative of the laxity of the medial and of the lateral collateral ligaments, as these ligaments delimit knee laxity. When the posterior and the anterior cruciate ligaments have not been resected (e.g., in a cruciate retaining surgery), these ligaments may also affect laxity. The knee articular capsule and the patellar tendon may also affect joint laxity.

Figure 8D:
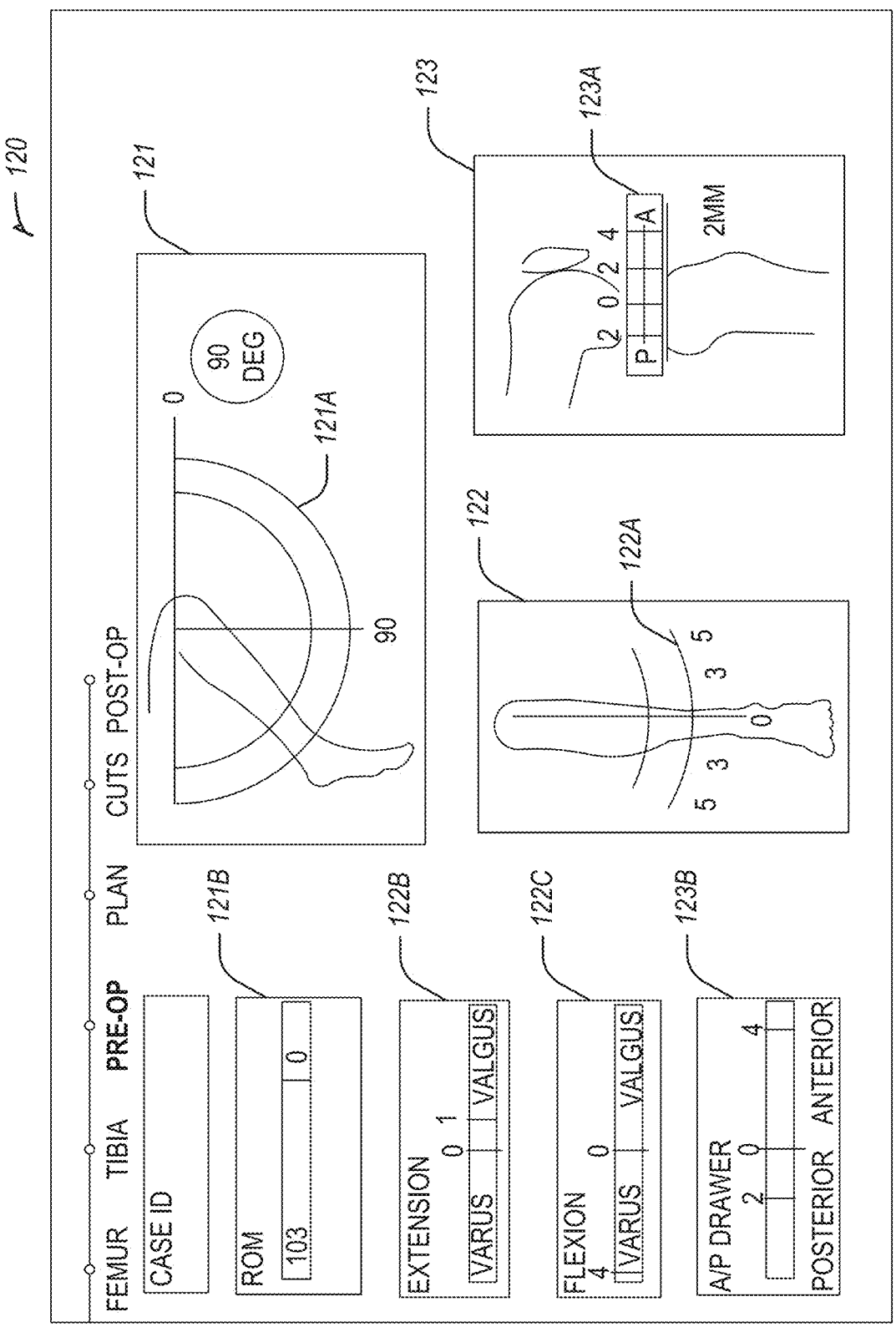

Referring to FIG. 8D, an enlarged joint display 123 may also be provided to visually illustrate the anterior and posterior drawer distances at flexion. To gather the information, with the leg flexed, the operator manually pushes and pulls the tibia relative to the femur to maximum posterior and anterior positions, and the tracking of the tibia and femur by the tracking device 70 allows the ROM analysis 53 to use the drawing positions, relative to a neutral position at which the tibia is natively positioned relative to the femur by soft tissue tension. Again, the maximum distances may be determined by the operator's judgement as to when to stop the pushing and pulling based on the resistance felt. The joint display 123 may have different forms, using a distance scale 123A to visually show the range of movement, and a distance bar 123B, showing the numerical values of varus and valgus. These values are recorded for subsequent use during the soft tissue balancing 56. Joint displays 123A and 123B may also indicate a target laxity (for comparison) which is programmed to reflect the ideal laxity. The ideal laxity may be based on a surgeon-defined preference or suggested value from literature.

Therefore, at the outset of the surgical workflow steps guided by GUI 120, the system 10 has recorded joint laxity data. The recorded information may be based on force feedback felt by the surgeon manipulating the tibia relative to the femur, or may be the result of manipulations by robotized components using sensors A and output by the force measurement 52 when the robotized components are programmed to limit force values. The recorded range of motion and joint laxity information may include maximum flexion angle, maximum extension angle, range of motion, varus and valgus angle values at extension, at flexion, or at any desired angle, anterior drawer distance, posterior drawer distance. The recorded information may be as a function of 3D bone models B of the tibia and femur, or of other bones in different surgical procedures. The order of information gathering using the GUI 120 may be changed from the order described above.

Figure 8E:
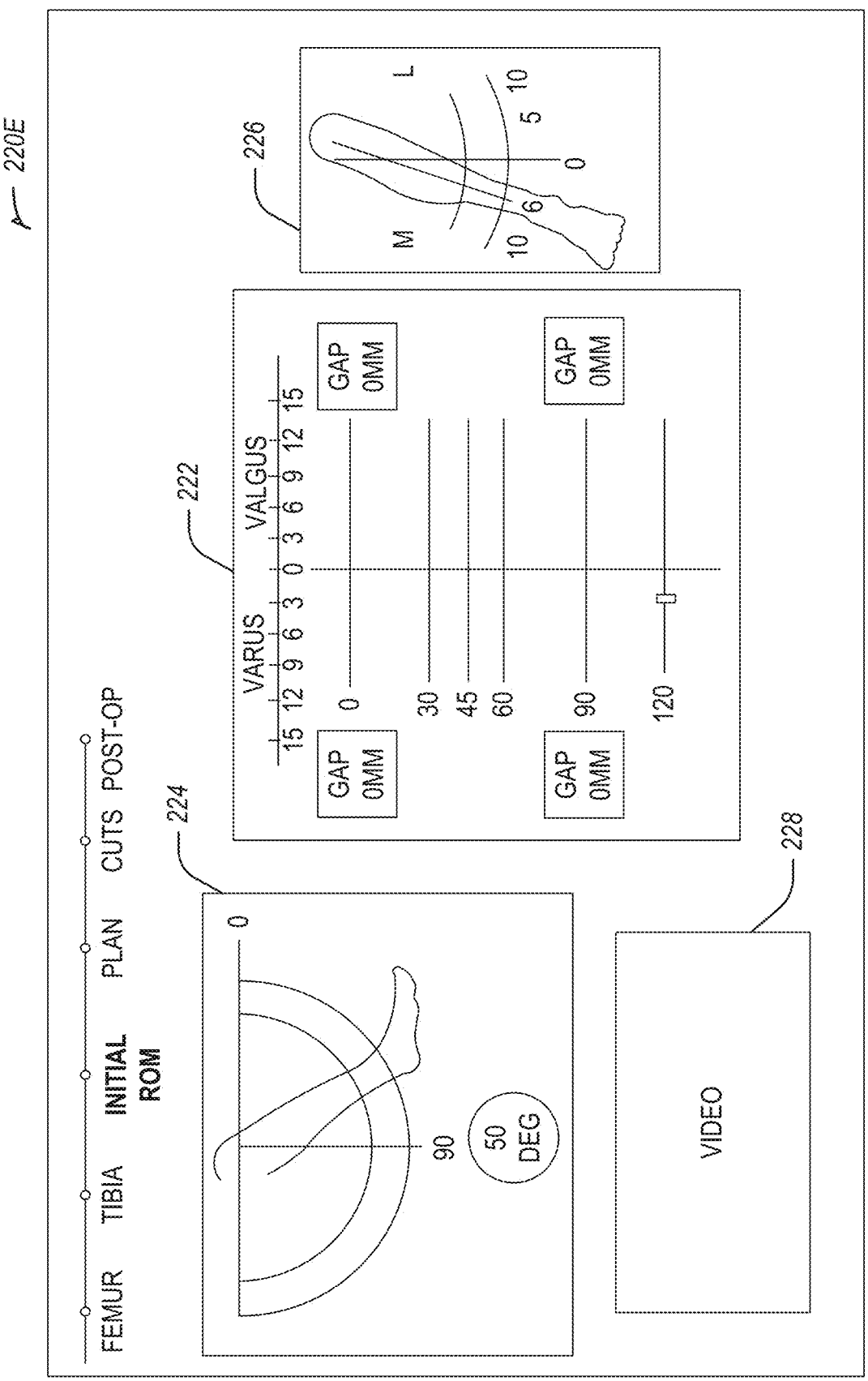
Figure 8F:
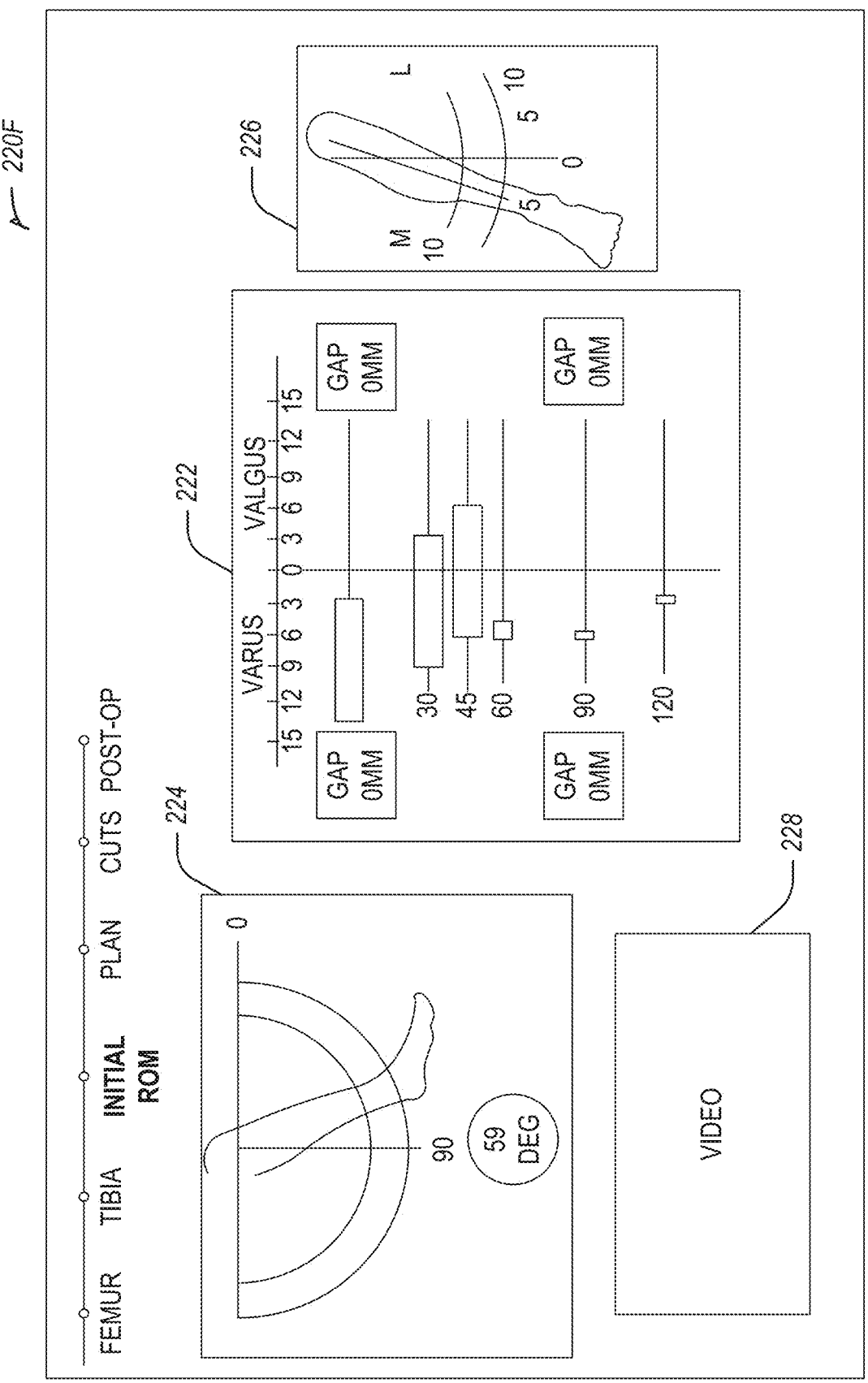

FIGS. 8E-8F illustrate some additional pre-operative graphical user interfaces (GUIs) 220A and 220B, which may be used for displaying flexion/extension angle, gaps, varus and valgus angles of a knee in accordance with some embodiments. The GUIs 220E and 220F include a video component 228 to display real-time range of motion. The GUIs 220E and 220F include one or more graphical information components. For example, GUI 220E shows the varus/valgus angle 226 at 6 degrees varus in the medial direction at a flexion angle 224 of 50 degrees (from full extension at 0 degrees). GUI 220F shows the varus/valgus angle 226 at 5 degrees varus in the medial direction at a flexion angle 224 of 59 degrees (from full extension at 0 degrees). Additional information is shown at graphical information component 222 in the GUIs 220E and 220F. The graphical information component 222 includes gap information, varus/valgus angle information, range of motion information, and extension/flexion information. The range of motion information may be used to create a preoperative plan.

In an example, one or more of the GUIs 220E or 220F may provide a remote video or allow for a remote audio connection, such as with a remote surgeon. The remote video or remote audio may be a real-time connection to allow the remote surgeon to discuss a procedure or provide training with a local surgeon or to monitor the local surgeon. A GUI used by the remote surgeon may provide the remote surgeon with a video display of a surgical field operated by the local surgeon.

Referring to FIGS. 9A and 9B, GUI 130 is used for the planning of the implant positions and orientations, taking into consideration joint laxity and range of motion as obtained using GUI 120. The GUI 130 receives output from the implant assessment 54 and from the soft tissue balancing 56. The GUI 130 may have a joint display 131 showing bone models B with implant models C. The joint display 131 may include a view of the knee in extension (FIG. 9A) and a view of the knee in flexion (FIG. 9B). According to an embodiment, the user of GUI 130 may toggle between flexion and extension views, and may also toggle between frontal (FIGS. 9A and 9B), sagittal or axial planes of view, on preference. The initial or proposed location of the implant models C relative to the bone models B may be determined by the implant assessment 54 using the joint laxity data output by the soft tissue balancing 56. The current location may be quantified using different markers, such as those described below. Joint-line variation plane 131A may display the pre-operative joint line versus the proposed joint line or the current joint line (i.e., actual location, as modified) when an operator varies the location of either one of the implant models C. Lateral laxity scale 132A and medial laxity scale 132B may provide a visual indication of the acceptable lateral and medial soft tissue tension. In FIGS. 9A and 9B, the acceptable range is indicated by upper and lower limits, along with a pointer indicating the tension at the current implant locations. The scales 132A and 132B may also provide gap distances, current femur and tibia varus/valgus angles, and an anterior gap for patellofemoral joint stuffing as additional data representative of joint laxity. The gap distances may be the sum of planned resection and ligament laxity compared to implant thickness. According to an embodiment, the laxity scales 132A and 132B dynamically reflect modifications to the planned implant location. The adjustments to implant location reflected on the laxity scales 132A and 132B may also be reflected by changes in the graphs shown in FIGS. 6B and 7B, as a function of a rotation of the implant. In other words, as the implant location or orientation is adjusted the varus/valgus balanced line 60 can shift, as discussed above in reference to FIGS. 6B and 7B. A femoral component window 133 may enable the change of femoral implant size. The user may have the possibility of changing implant sizes, in which case the displayed femoral implant model and related information on the joint display 131 may be updated (131A, 132A, 132B, etc.). A spacer component window 134 may enable the selection of the spacer thickness or the type of spacer. Changes to the spacer component may result in a dynamic update of the joint display 131 and of related data (131A, 132A, 132B, etc.). A tibial component window 135 may enable the change of tibial implant size, with the user given the option of changing implant sizes, in which case the displayed tibial implant model and related information on the joint display 131 may be dynamically updated (131A, 132A, 132B, etc.). A location control panel 136 is provided for the user to modify the location of the femoral component relative to the femur, in translation or location. As the location is modified using the location control panel 136, the joint display 131 may be updated and applicable data is also adjusted, such 131A, 132A, 132B, etc. Alternatively or additionally, the implants in the joint display 131 may be widgets that may be moved around relative to the bone models B, with the consequential dynamic adjustment of applicable data (e.g., 131A, 132A, 132B). The widget feature may be available in all views. It has the same function whether it is overlaid on the knee or on the left panel of GUI 130: it allows the user to position/orient the implant with respect to the bone. The effect of changing position or orientation of the implant will be dynamically reflected in the laxity scales. The laxity scales will be different in flexion and extension. The laxity scales could be provided throughout all angles of flexion.

Accordingly, the processor may perform the implant assessment 54 or the soft tissue balancing 56, and may propose implant components and locations for the implant components via the GUI 130. The GUI 130 gives the possibility to an operator to modify the implant components or their locations, by dynamically updating in real-time quantitative data related to joint laxity and range of movement, to assist the operator is finalizing the resection planning. When the implants are selected and their locations are set, the information of the GUI 130 is converted into another form of the output D, such as personal surgical instrument tool files or data to perform resection as decided, a navigation file for the robot arm 20 when present, or a navigation file for tracked tools. The GUI 130 may also be used post-resection, to provide the joint laxity data for the "as-resected" state. The data may be used to document the surgical procedure. This may also allow post-resection corrections when deemed necessary. It may be required to return to GUI 100 or 110 to recalibrate the bones to obtain more precision in the assessment.

FIGS. 10A-10D illustrate example user interfaces 330A-330D for joint replacement surgical planning in accordance with some embodiments. User interface 330A of FIG. 10A includes a cut checklist 332 to illustrate cuts that have been performed or that are not yet completed. User interface 330A includes an interactive user guide 334 showing a soft tissue balancing test overview. The user guide 334 shows a target implant rotation with respect to a femur to give a balanced flexion gap. The user guide 334 shows four steps of the soft tissue balancing test, from an initial state, to pulling on the femur, to showing a gap imbalance, to finally showing a rotation to align the soft tissue.

Figure 10A:
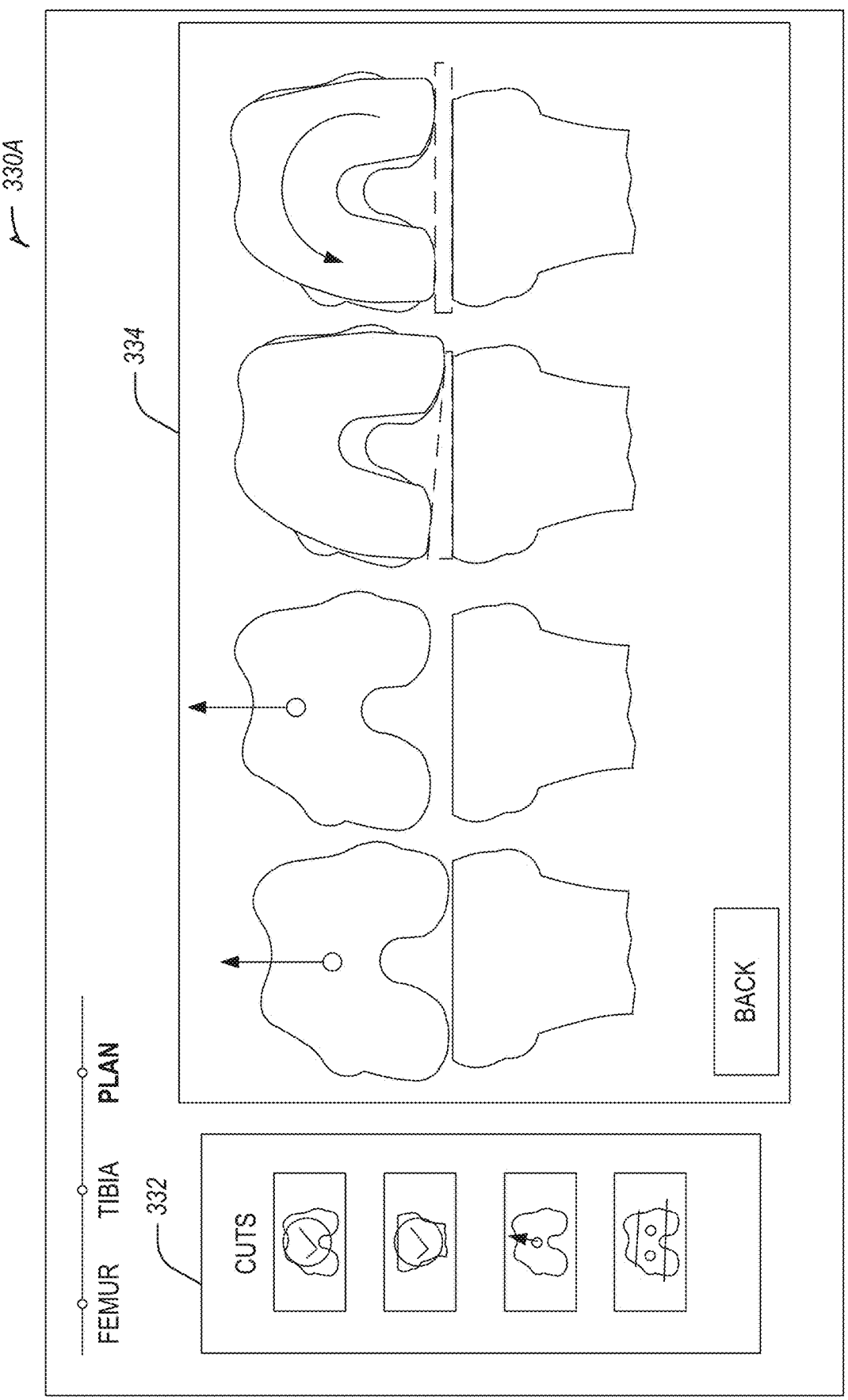
FIGS. 10A-10D illustrate example user interfaces for joint replacement surgical planning in accordance with some embodiments.
Figure 10B:
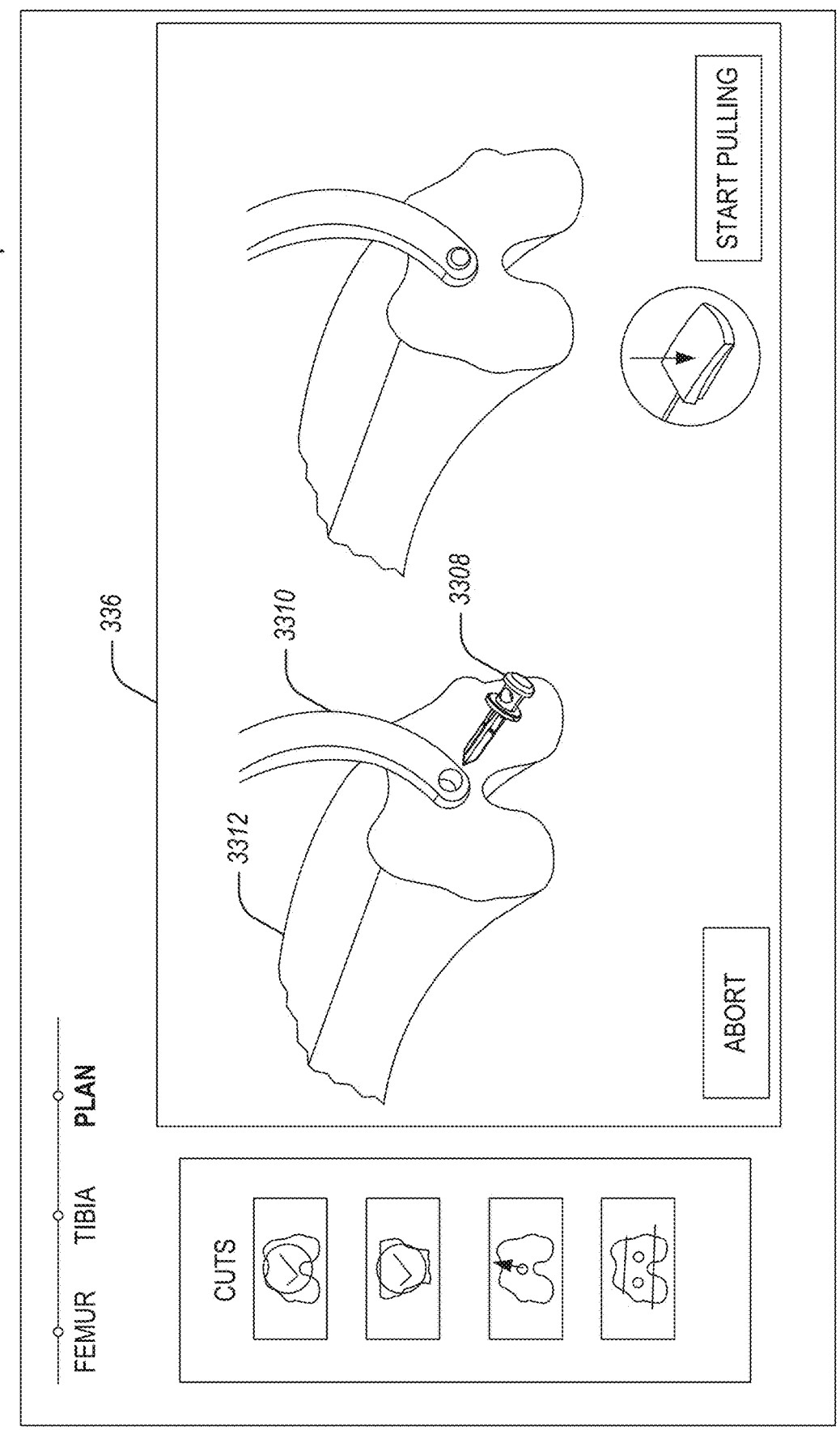

User interface 330B of FIG. 10B includes a second user guide 336 including instructions on how to insert a spike 3308 to connect a soft tissue balancing component 3310 to a femur 3312. The spike 3308 holds the soft tissue balancing component 3310 in place, but may allow the femur 3312 to rotate. The soft tissue balancing test may be initiated, for example, by pressing a foot pedal, which is indicated in the second user guide 336. In an example, the soft tissue balancing test may be performed with a patella or soft tissue in place by using a j-shaped or hook-shaped soft tissue balancing component 3310. When the soft tissue balancing test is initiated, a robotic arm may pull the soft tissue balancing component 3310, such as by using an end effector connecting the robotic arm to the soft tissue balancing component 3310 to apply a force on the spike 3308, which may in turn cause a force on the femur 3312, for example to move the femur 3312 away from a tibia.

Figure 10C:
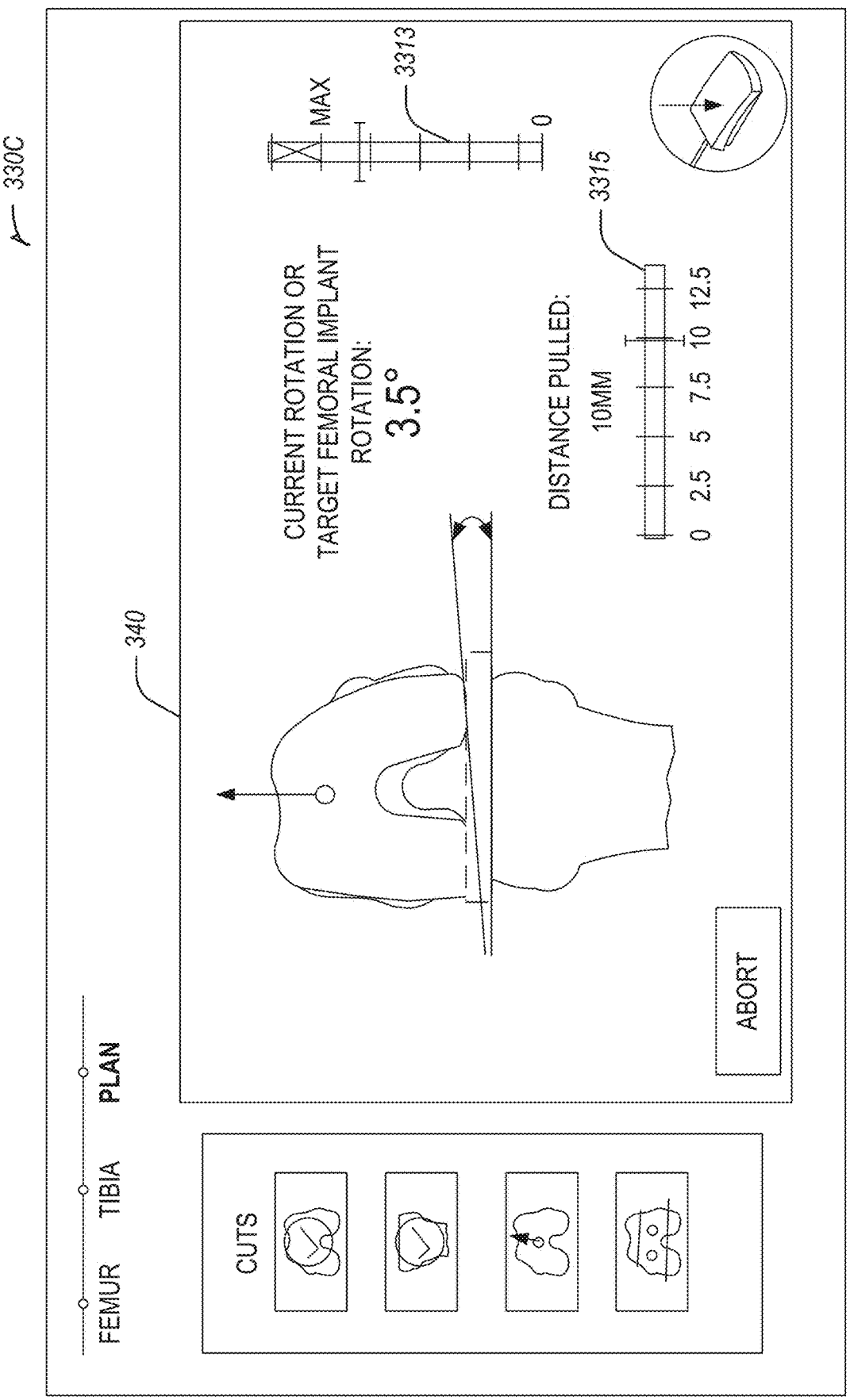

User interface 330C of FIG. 10C includes a third user guide 340 which shows an illustration of a patient joint including a current imbalance at a particular gap distance, while superimposing a proposed balance (e.g., based on completed releases, cuts, and implants added to the joint). The third user guide 340 includes information related to a current rotation or a target femoral implant rotation (e.g., the rotation information may change over time or during a procedure, such as from a current rotation to a target rotation, or may show both, or a difference). The distance pulled (e.g., over time or at a current time) is also illustrated in the third user guide 340. The third user guide 340 may include user-selectable options to apply a target femoral implant rotation to a 3D plan or to not apply the target femoral implant rotation to the 3D plan. The 3D plan may include preoperative or intraoperative plans. Adding the target femoral implant rotation to the 3D plan may include adding it to the 3D plan as is, or with changes (e.g., surgeon adjustments).

The user guide 340 may include a force bar 3313 or a distance bar 3315. The force bar 3313 may be used to display a current pulling force (e.g., of a robotic arm on the femur). In an example, the robotic arm may be stopped automatically by a robotic controller when the force reaches a maximum force, which may be displayed on the force bar 3313. In an example, a surgeon may control the robotic arm by adjusting the force bar 3313. The distance bar 3315 may move simultaneously with the force bar 3313 in an example. The distance bar 3315 shows a distance pulled, such as a distance from the femur to the tibia (whether the femur or the tibia is pulled). In an example, the distance bar 3315 may be controlled by a surgeon to move the robotic arm similar. In an example, the distance bar 3315 may include a maximum distance pulled, which when the femur and the tibia are separated by the maximum distance, the robotic arm may be stopped.

Figure 10D:
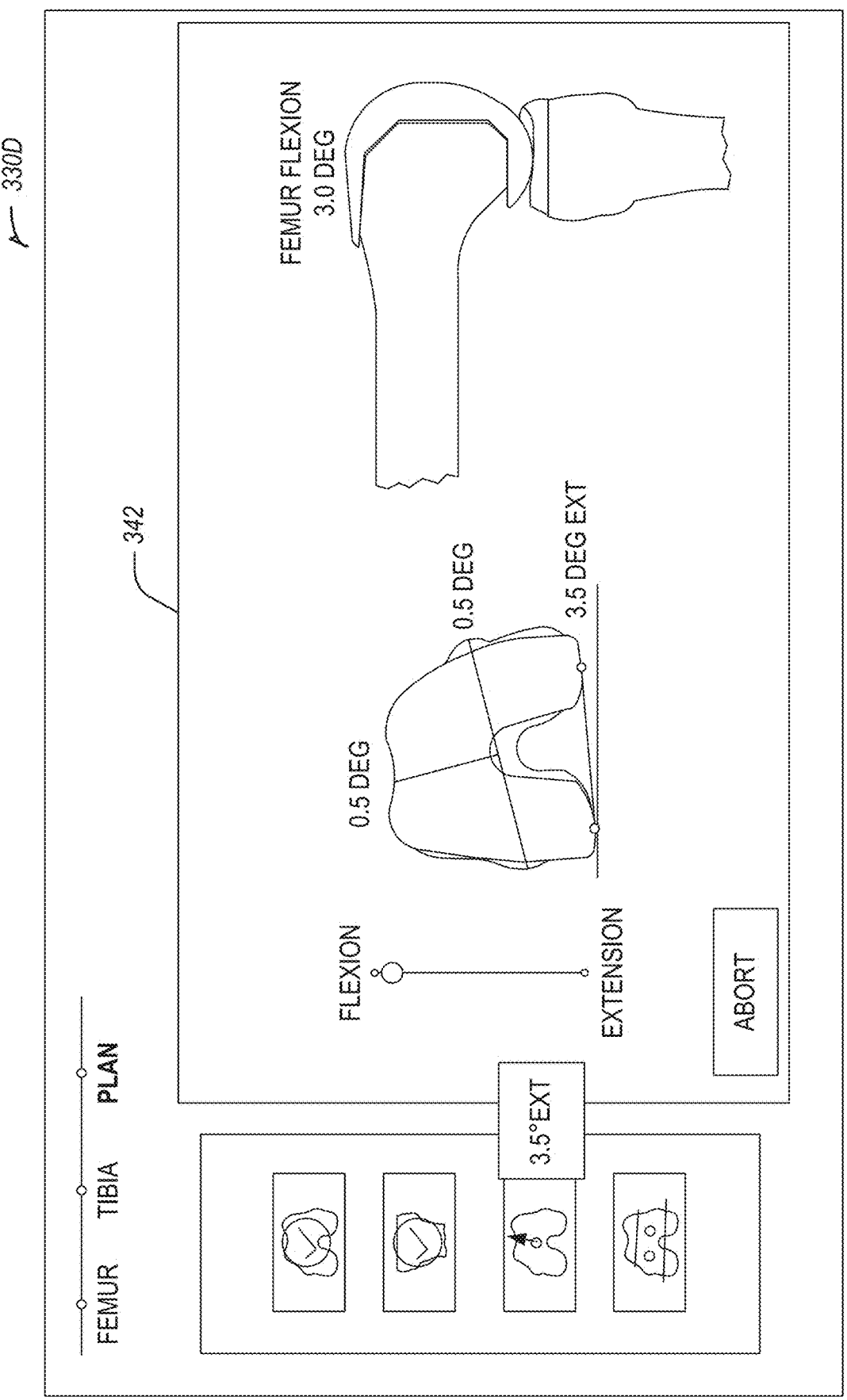

User interface 330D of FIG. 10D includes a fourth user guide 342, which shows rotation of a femur in a knee joint in various views. The femur may be viewed in flexion with respect to a tibia or in extension. When used intraoperatively, as the joint is placed in these different orientations, the user guide 342 may be automatically updated (e.g., using trackers).

One or more of user guides 334, 336, 340, or 342 may include information on ligament balance. For example, a soft tissue balancing test may be performed, and force information, tension information, or other sensor data may be sent to the one or more of user guides 334, 336, 340, or 342 to display soft tissue balance, such as a rotation angle to balance the ligaments. In another example, the one or more of user guides 334, 336, 340, or 342 may display a measured resection technique, for example by providing feedback on actual measured angles or detected forces after or before resection, in addition to the rotation angle at which there is balance.

In an example, medial and lateral borders of a tibial tubercle may be identified and used to determine a medial third landmark location. The one or more of user guides 334, 336, 340, or 342 may display the medial and lateral borders or the medial third landmark location. For example, a robotic arm may be used to identify a most medial boundary of a tibial tuberosity. The robotic arm may be used to identify a most lateral boundary of the tibia tuberosity. A system may use these identified boundaries to accurately display and locate a location known as a medial third location on the tibial tuberosity. Identifying this location may not be reproducibly performed with conventional instrumentation, such as with sub-millimeter metric precision. This location may be used to assist in a rotational placement of a tibial base plate for a knee arthroplasty as a reference point.

FIGS. 11A-11E illustrate graphic-user interfaces (GUI) for soft-tissue balancing and implant placement in accordance with some embodiments. The user guides 400A-400B (collectively referred to as GUI 400) provide an alternative interface for selecting implant location and orientation as well as a graphical representation of soft-tissue balance based on implant size, orientation, and location. The GUI 400 includes a soft-tissue section 425 (425A-425E, collectively referenced as soft-tissue section 425) that provide a surgeon or surgical assistance an informative view of a predicted condition of the joint (a knee joint in the examples illustrated). The soft-tissue section 425 can include a trapezoidal graphic 430 (trapezoidal graphic 430A-430E, collectively referenced as trapezoidal graphic 430) positioned between graphics representing a distal femur 426 and proximal tibia 427. The trapezoidal graphic 430 is an interactive element that updates in response to inputs adjusting parameters such as implant position (medial-lateral, anterior-posterior), implant orientation (varus/valgus rotation), and spacer size selection, which can all be a function of or affect soft-tissue tension and/or balance in the joint. The trapezoidal graphic 430 is designed to reproduce what the surgeon is seeing within the joint under reconstruction, while overlaying quantitative information, such as gap distance (medial-lateral), cut depths (medial-lateral), laxity measurements (medial-lateral), distal femur resection angle, posterior femoral resection angle, proximal tibia resection angle, and spacer size representation. The trapezoidal graphic 430 does not specifically illustrate a proximal tibia resection angle, but this can be displayed in a manner similar to the distal femur resection angle. For example, the bottom line of the joint gap indicator 432A can include an angled portion to indicate an angle of the proximal tibial resection.

Figure 11A:
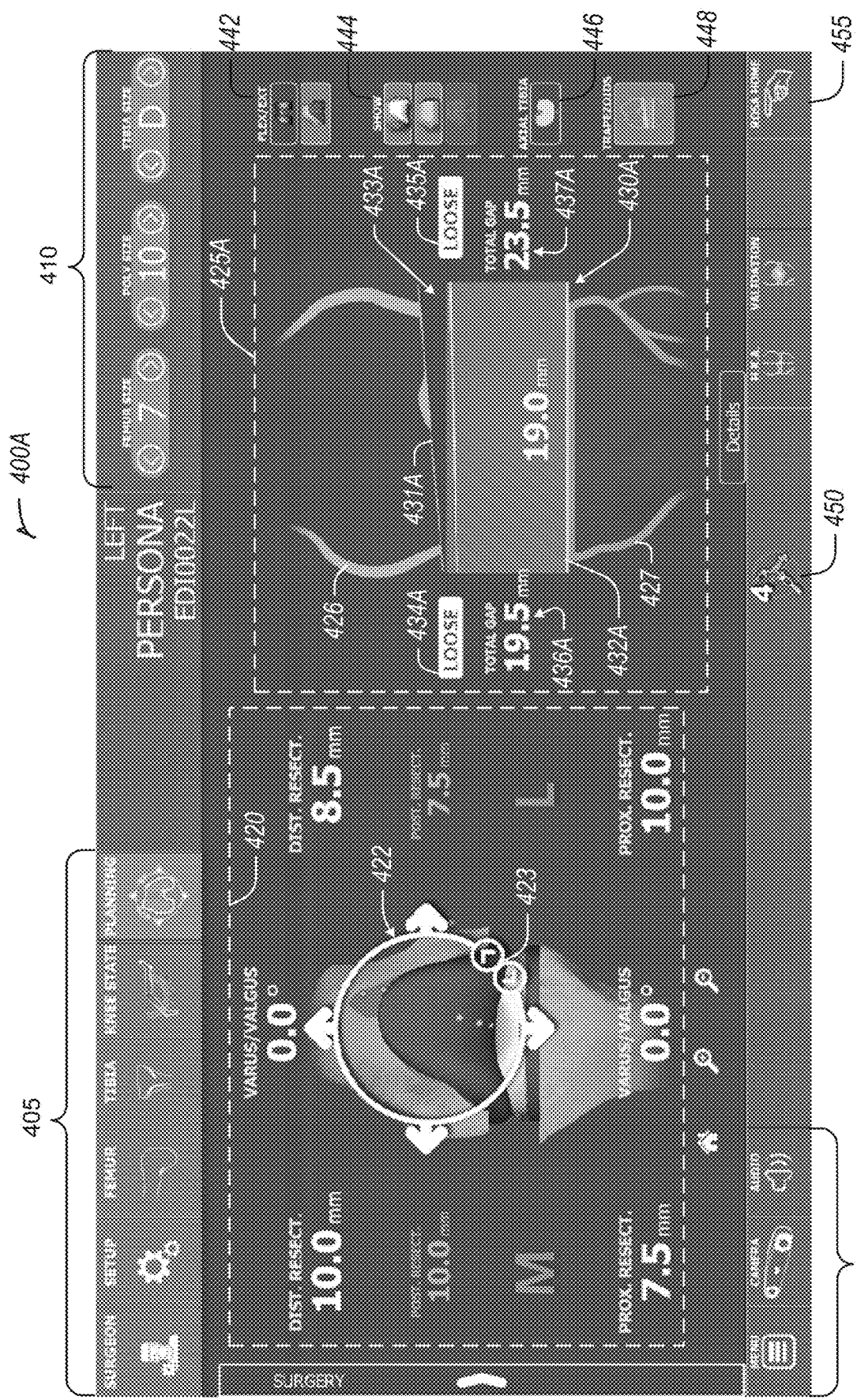
FIGS. 11A-11E illustrate graphic-user interfaces (GUI) for soft-tissue balancing and implant placement in accordance with some embodiments.

In the example illustrated in FIG. 11A, the GUI 400A includes a surgical procedure guide 405, a size selection interface 410, a system menu 415, an implant positioning section 420, a soft-tissue section 425A, flexion/extension control 442, display control 444, a bone view control 446, a trapezoid control 448, a tracking system control 450, and home control 455. In this example, the joint is illustrated in extension with the flexion/extension control 442 highlighting the extension selection. The implant positioning section 420 can include a position control 422 that enables the surgeon to adjust medial-lateral and anterior-posterior position of the implant. The implant positioning section 420 can also include an orientation control 423, which enables the surgeon to adjust varus/valgus angle of the implant. The implant positioning section 420 can also include various numeric or textual readouts to provide the surgeon with quantitative information related to the surgical procedure based on the current implant position. In this example, the quantitative information displays include distal resection amount and proximal resection amount on both the medial and lateral sides. The example can also include medial and lateral posterior resection measurements (with flexion selected in the flexion/extension control 442). Finally, the implant positioning section 420, in this example, includes readouts for varus/valgus angles for femur and tibia. The position control 422 and orientation control 423 is illustrated over the femoral component, but can also be activated for the tibial component via selection of the tibial component.

In this example, soft-tissue section 425A includes distal femur graphic 426, proximal tibia graphic 427, trapezoidal graphic 430A, balance angle indicator 431A, joint gap indicator 432A, resection angle indicator 433A, medial laxity indicator 434A, lateral laxity indicator 435A, medial gap data 436A, and lateral gap data 437A. In this example, the trapezoidal graphic 430A includes the balance angle indicator 431A, the joint gap indictor 432A, and the resection angle indicator 433A. The balance angle indicator 431A can provide a graphical representation of how soft tissue in the joint is balanced based on a calculated position and angle of a femoral resection based on a selected implant position and orientation. The resection angle indicator 433A, in this example, graphically illustrates the angle of the distal femoral resection, which is related to the balance angle indicator 431A. In examples illustrating the joint in flexion, the resection angle indicator 433A displays a resection angle of a posterior femoral resection. In certain examples, the resection angle indictor 433A can be color coded and/or displayed with a textual indication of angle. The joint gap indicator 432A graphically (and textually in this example) illustrates the common gap across the medial-lateral width of the joint. In some example, the joint gap indicator 432A provides an indication of the space available for implants and/or spacer components. For example, the joint gap indicator 432A can illustrate and/or indicate a calculated spacer size, which may or may not also represent the common gap distance. Other components in the joint prosthesis will take up a portion of the total gap distance, such as the femoral component and the tibial tray.

Figure 11B:
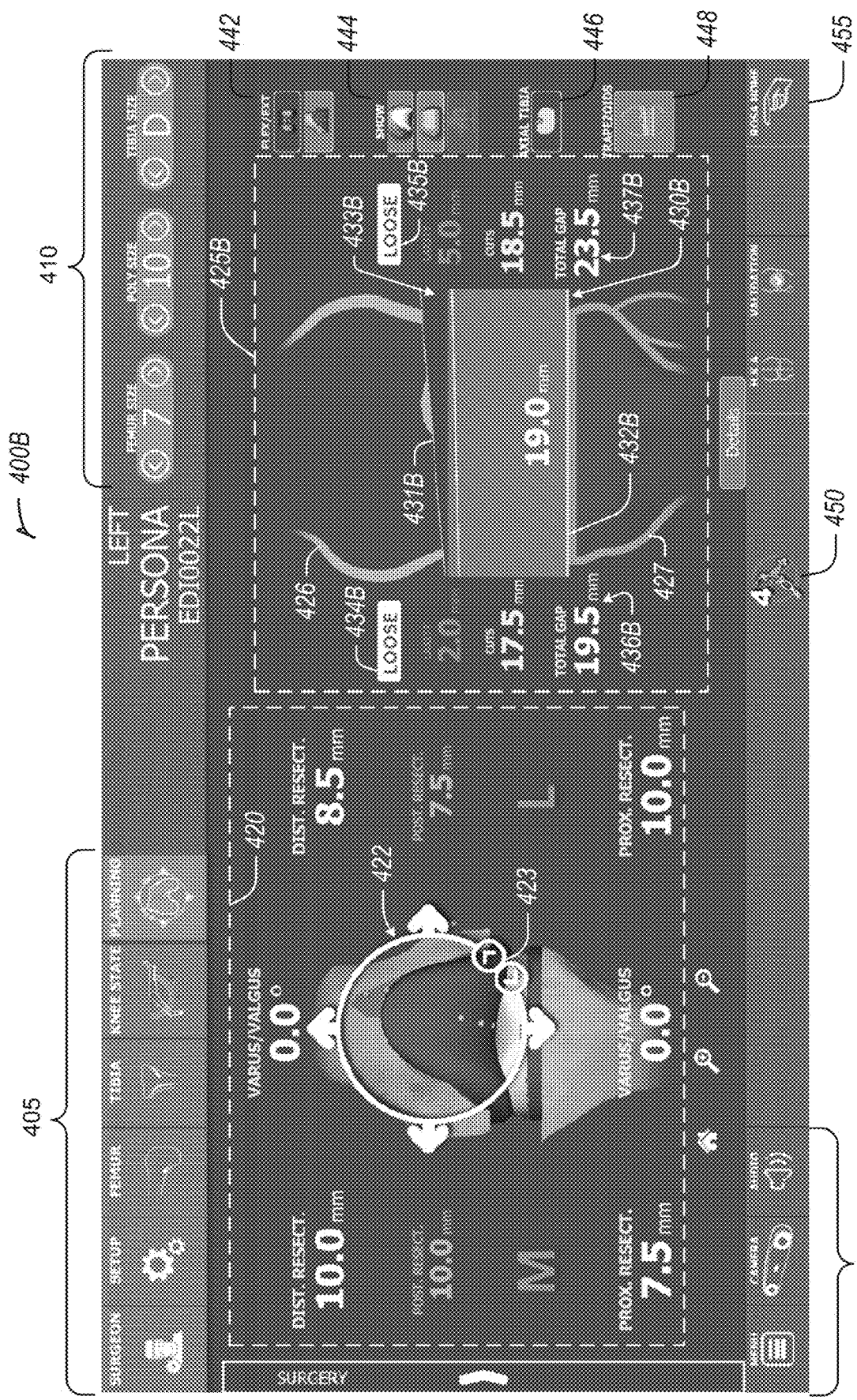

FIG. 11B illustrates another example GUI 400B with a modified collection of information displayed in the soft-tissue section 425B. In this example, the soft-tissue section 425B includes trapezoidal graphic 430B, medial laxity indicator 434B, lateral laxity indicator 435B, medial gap data 436B, and lateral gap data 437B. In this example, the trapezoidal graphic 430B includes joint gap indicator 432B, balance angle indicator 431B and resection angle indicator 433B as well as a textual display indicating the common gap distance across both medial and lateral side of the joint (19.0 mm in this example). The medial gap data 436 and lateral gap data 437B both include information such as Total Gap and Cut measurements. The medial laxity indicator 434B and the lateral laxity indicator 435B both include readouts indicating actual laxity measurement in addition to the Loose, Normal, or Tight indictors.

Figure 11D:
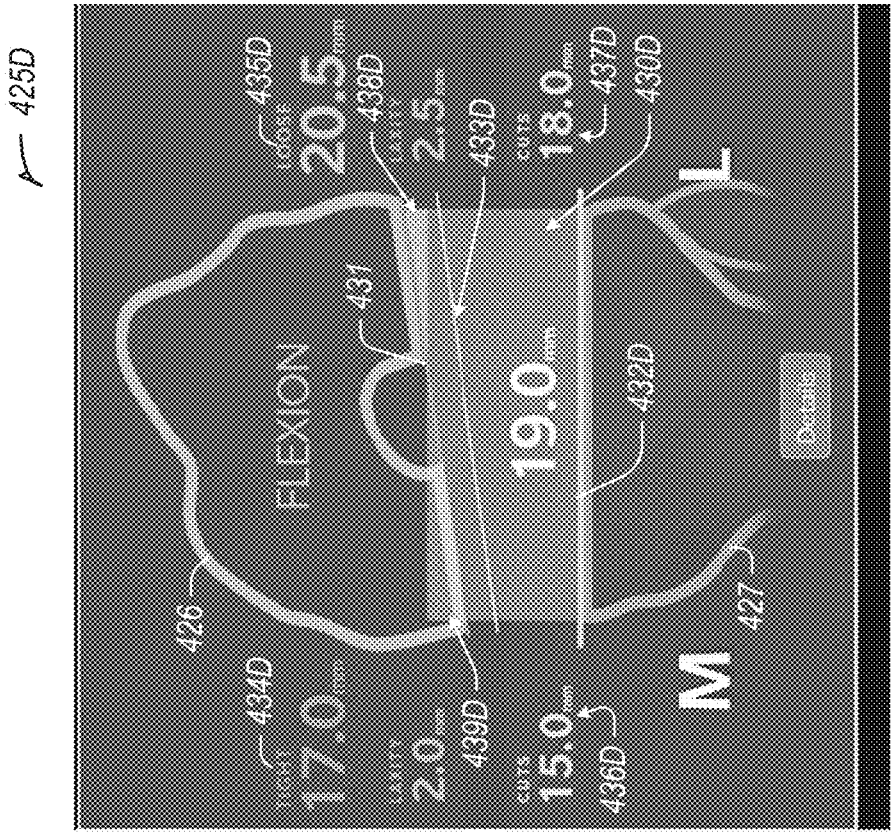
Figure 11C:
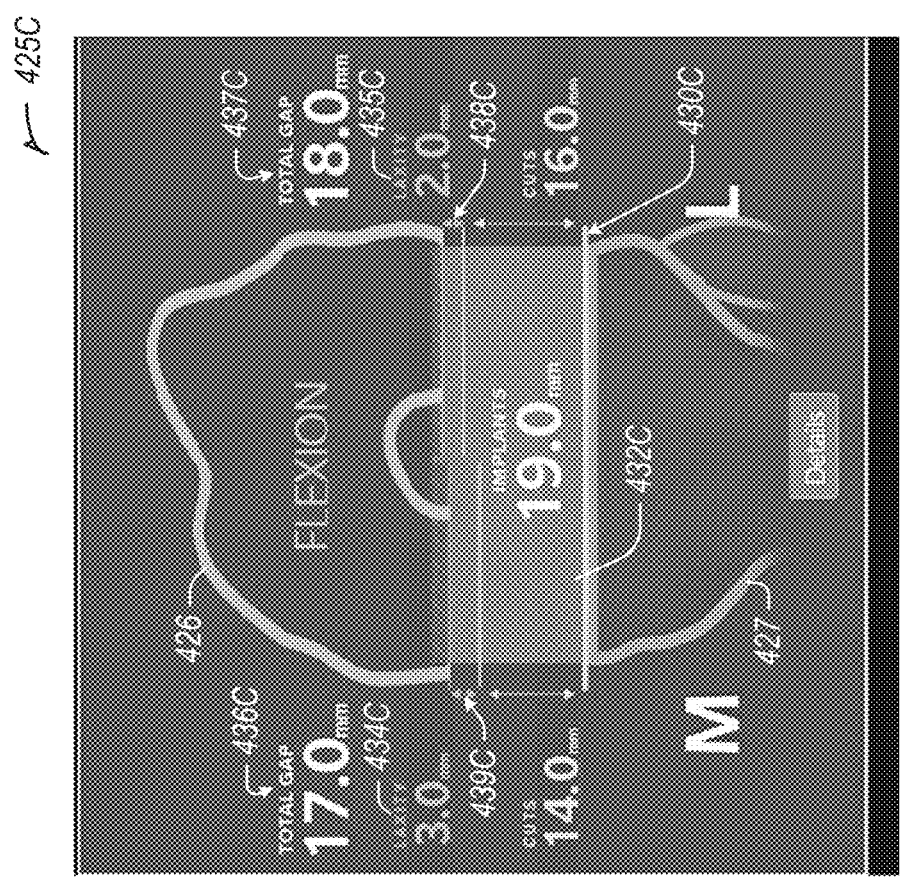

FIG. 11C illustrates another example soft-tissue section portion of the GUI 400 discussed in the previous two figures. In this example, the knee joint is in flexion, which means the femoral resection displayed is a posterior resection. The soft-tissue section 425C can include trapezoidal graphic 430C, medial laxity indicator 434C, lateral laxity indicator 435C, medial gap data 436C, and lateral gap data 437C. In an example, the trapezoidal graphic 430C can include a joint gap indicator 432C, medial overlap indicator 439C and lateral overlap indicator 438C. The medial overlap indicator 439C provides a linear graphical display of the medial condyle overlap into the projected posterior femoral resection. In this example, the angle of the resection is not depicted, but rather a bar-graph type view of the overlaps of the condyles is shown instead. The lateral overlap indicator 438C depicts the lateral condyle overlap. The hashed portion of the medial overlap indicator 439C and lateral overlap indicator 438C illustrate the amount of laxity on each side of the joint illustrated in conjunction with the condyle overlap to assist in putting the laxity measurements into perspective in view of the planned resections.

FIG. 11D illustrates another example soft-tissue section including a variation on the trapezoidal graphic with the knee joint in flexion. In this example, trapezoidal graphic 430D can include balance angle indicator 431D, joint gap indicator 432D, resection angle indicator 433D, lateral overlap indicator 438D and medial overlap indicator 439D. The lateral overlap indicator 438D and the medial overlap indicator 439D in this example are angled to coincide with the resection angle indicator 433D. Additionally, the direction and coloring of the hashed portion of the lateral overlap indicator 438D and the medial overlap indicator 439D provide information on joint laxity. For example, the lateral overlap indicator 438D is illustrated as being above the joint gap indicator 432D, which can indicate a loose portion of the joint. In some example, the hashed portion of the lateral overlap indicator 438D can be colored green if the looseness is considered acceptable or desirable. In other examples, a different color may be utilized to indicate a loose joint, such as orange. In this example, the medial overlap indicator 439D is depicted as below the upper portion of the joint gap indicator 432D, and may be colored red to indicate a negative overlap or an undesirable condition. Again, a different (more neutral) color may be associated with a negative overlap to indicate a tight joint section (especially where the tightness is not considered undesirable). The coloring in particular of these graphical displays can be configured to correspond to a surgeon's preferences in terms of joint laxity measurements. For example, a surgeon may never want to see a tight joint, so any tight indicator may always be colored red to assist in quick identification of an undesirable condition. Any of the soft-tissue sections discussed can utilize colored graphics and/or text to indicate positive, negative, or neutral conditions of a joint under reconstruction. The surgeon can program parameters of the GUI to conform to individual preferences for joint soft-tissue balance, resection depths, and spacer sizing, among other things.

Figure 11E:
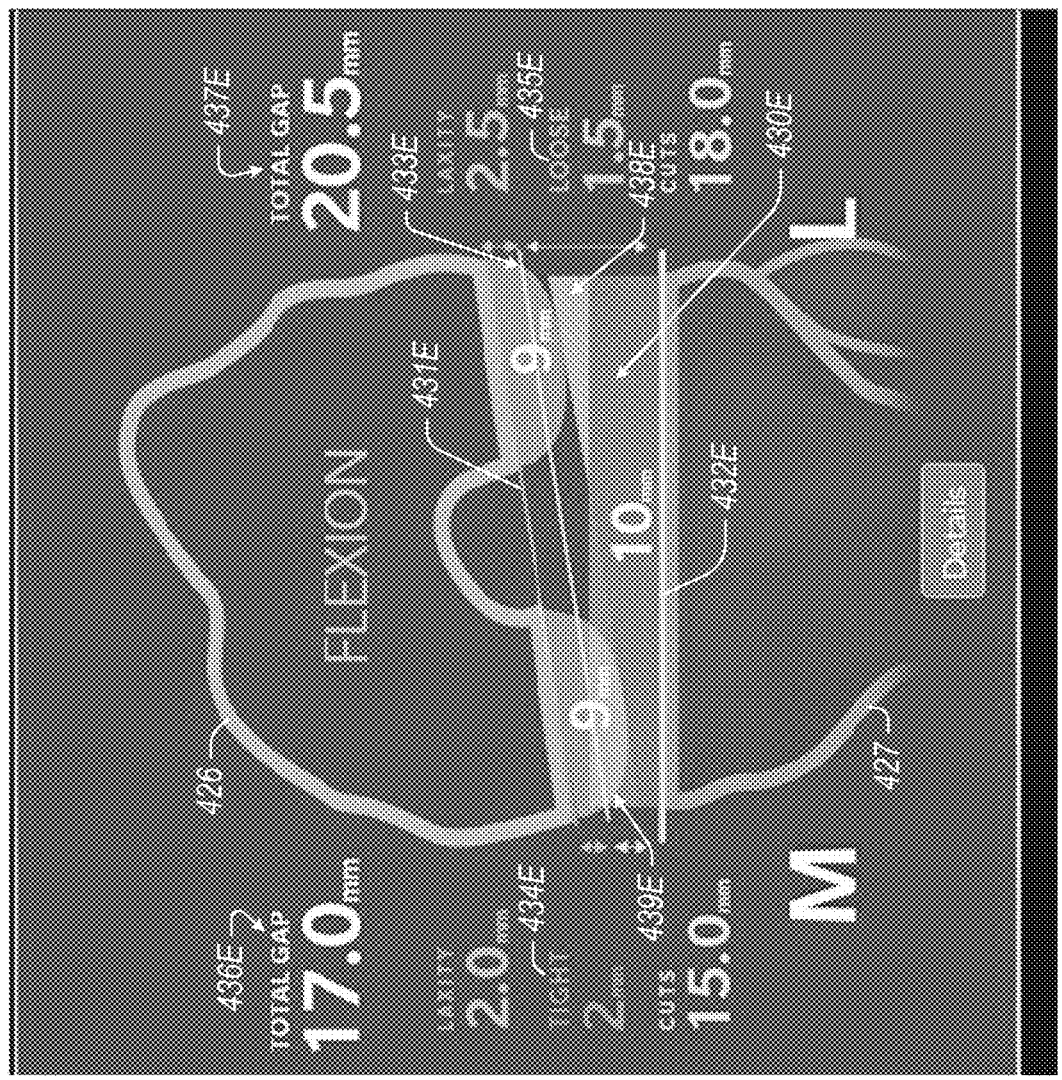

FIG. 11E illustrates another example soft-tissue section including a variation on the trapezoidal graphic. In this example, trapezoidal graphic 430E can include balance angle indicator 431E, joint gap indicator 432E, resection angle indicator 433E, lateral overlap indicator 438E and medial overlap indicator 439E. The lateral overlap indicator 438E and the medial overlap indicator 439E in this example are angled to coincide with the resection angle indicator 433D and a graphical representation of the posterior portions of the medial and lateral condyles is also included in the distal femur graphic 426. Also in this example, the medial laxity indicator 434E and the lateral laxity indicator 435E include Loose/Neutral/Tight indicators as well as total laxity measurements and measures of tightness or looseness. In this example, the medial laxity indicator 434E indicates a tight joint side with 2.0 mm of total laxity and 2 mm of tightness. While the lateral laxity indicator 435E indicates a loose joint side with 2.5 mm of total laxity and 1.5 mm of looseness. In this example, the medial laxity indicator 434E may be color coded red to indicate tightness, which may also indicate that the displayed values are (or could be considered) negative numbers.

Figure 12:
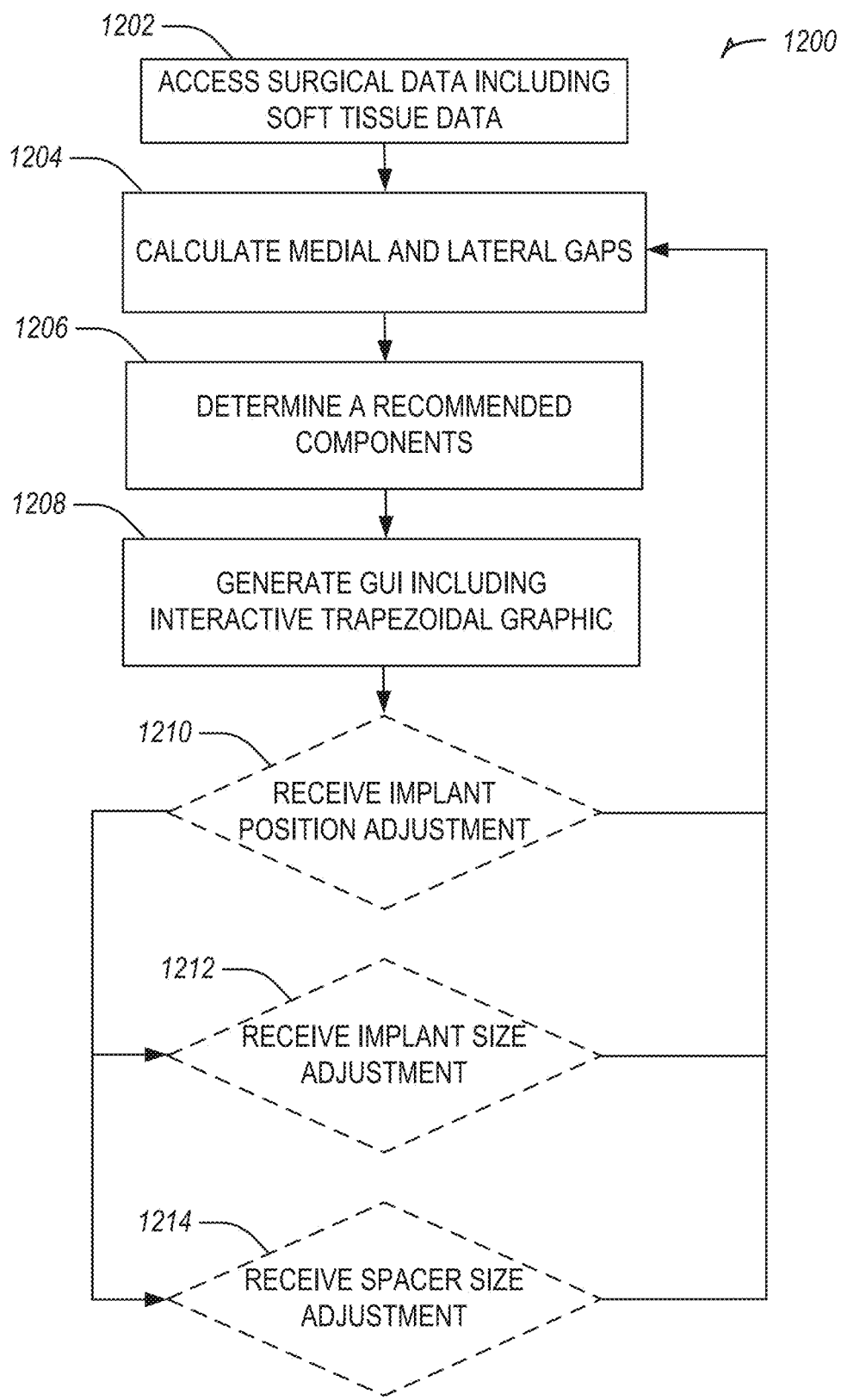
FIG. 12 illustrates a flow chart showing a technique for analyzing soft-tissue balance and adjusting implant placement in accordance with some embodiments.

FIG. 12 illustrates a flow chart showing a technique 1200 for analyzing soft-tissue balance and adjusting implant placement in accordance with some embodiments. In this example, the technique 1200 can include operations such as accessing surgical data at 1202, calculating gaps at 1204, determining components at 1206, generating the GUI at 1208, and optionally updating based on receiving inputs such as implant adjustment, implant size selection or spacer size adjustment. In an example, the technique 1200 can begin at 1202 with the controller 50 accessing surgical data including soft-tissue data. The soft-tissue data can include actual measurements of tension in a medial and a lateral side of joint. The soft-tissue data can also (or alternatively) include gap distance measurements taken when the joint is a particular position with a known tension or force applied. For example, the soft-tissue data can be measurements performed with the knee in flexion with a known force applied to displace either the distal femur or the proximal tibia in a direction to extract the joint. Note, soft-tissue measurements can be taken before or after initial resections of the distal femur and/or the proximal tibia.

At 1204, the technique 1200 can continue with the controller 50 calculating medial and lateral gaps based on the soft-tissue data received at operation 1202. In certain examples, the controller 50 utilizes tension measurements for the medial and lateral sides to estimate a gap distance for each side of the joint. Alternatively, the calculation of the gaps may involve resolving position data received from a robot or similar sensors to determine gap distances on the medial and lateral sides. In certain examples, the data used can include a distance and angle, where the distance is the distraction distance between the distal femur and proximal tibia and the angle is the measured angle of the proximal femur (in reference to the joint mechanical axis or the proximal tibia).

At 1206, the technique 1200 can continue with the controller 50 determining a recommended component set. The component (implant) set can include a femoral component, a tibial component, and a spacer. The component recommendation is determined, at least in part, based on the soft-tissue data as well as an understanding on the available component and spacer sizes within the implant system or kit.

Component select is also impacted by additional factors, such as size of distal femur and proximal tibia, among other things. Spacer size selection takes into account the size of implant selected, when determining how best to fit the gap with a combination of femoral component, tibia component and spacer (when necessary). The component selection is also impacted by the target soft-tissue tension or laxity measurement. The parameters associated with component selection, such as target laxity, can be surgeon preference driven allowing individual preferences to be built into the automated recommendations. Certain components can be selected in advance, such as femoral component and/or tibial component, in these examples the spacer size is calculated to attain target soft-tissue balance.

The technique 1200 can continue at 1208 with the controller 50 generating a GUI including an interactive trapezoidal graphic, such as trapezoidal graph 430. As discussed above, the trapezoidal graphic is generated to graphically illustrate soft-tissue and joint condition based on soft-tissue tension under circumstances predicted with selected implants and/or spacers. The trapezoidal graphic is interactive; in that it changes or updates as parameters of the implant or spacer are changed. For example, the technique 1200 can optionally include at 1210 with the controller 50 receiving an implant position (or orientation) adjustment. Upon receipt of the implant position adjustment, the controller 50 returns to operation 1204 to recalculate and update the trapezoidal graphic at operation 1208. Further, the technique 1200 can optionally include the controller 50 receiving an implant size adjustment, which also results in recalculation of the trapezoidal graphic at 1208. Finally, the technique 1200 can optionally include operation 1214 where the controller 50 can receive a spacer size adjustment and re-process data to re-generate the trapezoidal graphic at 1208.

VARIOUS NOTES & EXAMPLES

Each of these non-limiting examples may stand on its own, or may be combined in various permutations or combinations with one or more of the other examples.

Example 1 describes subject matter that can include an intraoperative surgical system. The intraoperative surgical system can include a display device and a computing device coupled to the display device. The computing device can also include a processor coupled to a memory device, with the memory device including instructions that, when executed by the processor, cause the computing device to perform operations. The operations performed by the computing device can include accessing surgical data, calculating a medial total gap and a lateral total gap, calculating a recommended component set, generating a trapezoidal graphic within a graphical user interface, and outputting the graphical user interface to the display device. In this example, the surgical data can include soft tissue data indicative of at least tension in soft tissues surrounding a surgical location. Calculating a medial total gap and a lateral total gap is based at least in part on the soft tissue data. The component set is recommended based at least in part on the medial total gap and lateral total gap. The graphical user interface includes an interactive trapezoidal graphic overlaid onto a graphical representation of a distal femur and a proximal tibia. The interactive trapezoidal graphic can include a graphical representation of the medial total gap, the lateral total gap, and at least a portion of the recommended component set.

In Example 2, the subject matter of Example 1 can optionally include the interactive trapezoidal graphic having a balance angle indicator across the graphical representation of the distal femur at an angle representative of a difference between the medial total gap and the lateral total gap.

In Example 3, the subject matter of any one of Examples 1 or 2 can optionally include the trapezoidal graphic having a rectangular region representing a recommended spacer size of the recommended component set, the recommended spacer size is illustrated adjacent the graphical representation of the proximal tibia.

In Example 4, the subject matter of any one of Examples 1 to 3 can optionally include the instructions further including instructions that cause the computing device to calculate a plurality of resections, and the graphical user interface including indications of the plurality of resections.

In Example 5, the subject matter of any one of Examples 1 to 4 can optionally include the instructions further including instructions that cause the computing device to calculate a medial laxity and a lateral laxity, and the graphical user interface having a medial laxity indicator providing an output representative of the medial laxity and a lateral laxity indicator providing an output representative of the lateral laxity.

In Example 6, the subject matter of Example 5 can optionally include calculating the medial laxity and the lateral laxity using a set of laxity thresholds including a loose threshold and a tight threshold, and the medial laxity indicator and lateral laxity indicator can include a loose indication if the loose threshold is transgressed and a tight indication if the tight threshold is transgressed.

In Example 7, the subject matter of any one of Examples 1 to 6 can optionally include generating the graphical user interface with the interactive trapezoidal graphic by updating the interactive trapezoidal graphic responsive to adjustments in at least one of a position of an implant, a position of a planned resection, an implant size, and a spacer size selection, wherein the implant, the implant size, and the spacer size are included in the recommended component set.

In Example 8, the subject matter of Example 7 can optionally include generating the graphical user interface including generating user input controls for selection of at least one of an implant size and a spacer size.

In Example 9, the subject matter of Example 8 can optionally include generating the user input controls including generating an indexing control including an increase size input and a decrease size input.

In Example 10, the subject matter of Example 7 can optionally include generating the graphical user interface including generating position input controls to receive user input to move a virtual planned position of an implant.

In Example 11, the subject matter of Example 10 can optionally include generating the position input controls including a medial index control, a lateral index control, a distal index control, a proximal index control, and a rotation control.

Example 12 describes subject matter involving a computer-implemented method for generating and displaying an intraoperative planning interface. In this example, the method can include operations such as accessing surgical data, calculating a medial total gap and a lateral total gap, calculating a recommended component set, generating a trapezoidal graphic within a graphical user interface, and outputting the graphical user interface to the display device. In this example, the surgical data can include soft tissue data indicative of at least tension in soft tissues surrounding a surgical location. Calculating a medial total gap and a lateral total gap is based at least in part on the soft tissue data. The component set is recommended based at least in part on the medial total gap and lateral total gap. The graphical user interface includes an interactive trapezoidal graphic overlaid onto a graphical representation of a distal femur and a proximal tibia. The interactive trapezoidal graphic can include a graphical representation of the medial total gap, the lateral total gap, and at least a portion of the recommended component set.

In Example 13, the subject matter of Example 12 can optionally include generating the graphical user interface including user input controls to receive user input selecting at least one of a femoral component position adjustment, a femoral component size adjustment, a tibial component size adjustment, and a spacer size adjustment.

In Example 14, the subject matter of Example 13 can optionally include receiving, via the user input controls, a femoral component position adjustment. This example can also include, in response to receiving the femoral component position adjustment, recalculating the medial total gap, the lateral total gap, and a recommended spacer size, and in response to the recalculating, updating the interactive trapezoidal graphic.

In Example 15, the subject matter of any one of Examples 13 or 14 can optionally include receiving, via the user input controls, a femoral component size adjustment, and in response to receiving the femoral component size adjustment, recalculating the medial total gap, the lateral total gap, and a recommended spacer size, as well as in response to the recalculating, updating the interactive trapezoidal graphic.

In Example 16, the subject matter of any one of Examples 13 to 15 can optionally include receiving, via the user input controls, a spacer size adjustment, and in response to receiving the spacer size adjustment, recalculating the medial total gap and the lateral total gap, as well as in response to the recalculating, updating the interactive trapezoidal graphic.

In Example 17, the subject matter of any one of Examples 12 to 16 can optionally include generating the graphical user interface including the interactive trapezoidal graphic including updating the interactive trapezoidal graphic responsive to adjustments in at least one of a position of a femoral component, a position of a planned resection, a femoral component size, a tibial component size, and a spacer size selection.

In Example 18, the subject matter of any one of Examples 12 to 17 can optionally include generating the interactive trapezoidal graphic including generating a balance angle indicator across the superior edge of the interactive trapezoidal to visually depict the soft tissue data.

In Example 19, the subject matter of any one of Examples 12 to 18 can optionally include calculating a medial laxity and a lateral laxity based at least in part on the soft tissue data. The example can also include generating the graphical user interface including a medial laxity indicator providing an output representative of the medial laxity and a lateral laxity indicator providing an output representative of the lateral laxity.

In Example 20, the subject matter of Example 19 can optionally include calculating the medial laxity and the lateral laxity including making a comparison against a set of laxity thresholds including a loose threshold and a tight threshold, and where the medial laxity indicator and lateral laxity indicator includes a loose indication if the loose threshold is transgressed and a tight indication if the tight threshold is transgressed.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. An intraoperative surgical system comprising:
    a display device;
    a computing device coupled to the display device, the computing device including a processor coupled to a memory device, the memory device including instructions that, when executed by the processor, cause the computing device to perform operations including:
    accessing surgical data including soft tissue data indicative of at least tension in soft tissues surrounding a surgical location;
    calculating, based at least in part on the soft tissue data, medial total gap and a lateral total gap;
    determining, based at least in part on the medial total gap and lateral total gap, a recommended component set;
    generating, for display on the display device, a graphical user interface including an interactive trapezoidal graphic overlaid onto a graphical representation of a distal femur and a proximal tibia, wherein the interactive trapezoidal graphic includes a graphical representation of the medial total gap, the lateral total gap, and at least a portion of the recommended component set; and
    outputting the graphical user interface to the display device,
    wherein the graphical representation of the medial total gap and the lateral total gap include separate displays for total gap measurement and cut measurement, and
    wherein generating the graphical user interface includes generation of a medial overlap indicator and a lateral overlap indicator overlaid onto the graphical representation of the distal femur and the proximal tibia within the interactive trapezoidal graphic.

2. The system of claim 1, wherein the interactive trapezoidal graphic includes a balance angle indicator across the graphical representation of the distal femur at an angle representative of a difference between the medial total gap and the lateral total gap.

3. The system of claim 1, wherein the trapezoidal graphic includes a rectangular region representing a recommended spacer size of the recommended component set, the recommended spacer size is illustrated adjacent the graphical representation of the proximal tibia.

4. The system of claim 1, wherein the instructions further include instructions that cause the computing device to calculate a plurality of resections; and
    wherein the graphical user interface includes indications of the plurality of resections.

5. The system of claim 1, wherein the instructions further include instructions that cause the computing device to calculate a medial laxity and a lateral laxity; and
  wherein the graphical user interface includes a medial laxity indicator providing an output representative of the medial laxity and a lateral laxity indicator providing an output representative of the lateral laxity.

6. The system of claim 5, wherein calculating the medial laxity and the lateral laxity includes comparison with a set of laxity thresholds including a loose threshold and a tight threshold; and
  wherein the medial laxity indicator and lateral laxity indicator includes a loose indication if the loose threshold is transgressed and a tight indication if the tight threshold is transgressed.

7. The system of claim 1, wherein generating the graphical user interface including the interactive trapezoidal graphic includes updating the interactive trapezoidal graphic responsive to adjustments in at least one of a position of an implant, a position of a planned resection, an implant size, and a spacer size selection, wherein the implant, the implant size, and the spacer size are included in the recommended component set.

8. The system of claim 7, wherein generating the graphical user interface includes generating user input controls for selection of at least one of an implant size and a spacer size.

9. The system of claim 8, wherein generating the user input controls includes generating an indexing control including an increase size input and a decrease size input.

10. The system of claim 7, wherein generating the graphical user interface includes generating position input controls to receive user input to move a virtual planned position of an implant.

11. The system of claim 10, wherein generating the position input controls includes a medial index control, a lateral index control, a distal index control, a proximal index control, and a rotation control.

12. The system of claim 1, wherein generating the graphical user interface includes user input controls configured to receive user input selecting at least one of a femoral component position adjustment, a femoral component size adjustment, a tibial component size adjustment, and a spacer size adjustment.

13. The system of claim 12, wherein generating the graphical user interface includes updating the interactive trapezoidal graphic upon receiving, via the user input controls, a femoral component position adjustment;
  wherein updating the interactive trapezoidal graphic includes recalculating the medial total gap, the lateral total gap, and a recommended spacer size based on the femoral component position adjustment.

14. The system of claim 12, wherein generating the graphical user interface includes updating the interactive trapezoidal graphic upon receiving, via the user input controls, a femoral component size adjustment;
  wherein updating the interactive trapezoidal graphic includes recalculating the medial total gap, the lateral total gap, and a recommended spacer size.

15. The system of claim 12, wherein generating the graphical user interface includes updating the interactive trapezoidal graphic upon receiving, via the user input controls, a spacer size adjustment;
  wherein updating the interactive trapezoidal graphic includes recalculating the medial total gap and the lateral total gap.

16. The system of claim 1, wherein the medial overlap indicator and the lateral overlap indicator depict a linear graphical display of condyle overlap into a projected posterior femoral resection.

17. The system of claim 1, wherein the medial overlap indicator and the lateral overlap indicator are bar-graph type views of condyle overlap into a projected posterior femoral resection.

18. Ari intraoperative surgical system comprising:
  a display device;
  a computing device coupled to the display device, the computing device including a processor coupled to a memory device, the memory device including instructions that, when executed by the processor, cause the computing device to perform operations including:
  generating, for display on the display device, a graphical user interface including an interactive trapezoidal graphic overlaid onto a virtual representation of a distal femur and a proximal tibia, the interactive trapezoidal graphic including graphical representations of measurements related to tension within soft tissues surrounding the distal femur and the proximal tibia as well as recommended resections to at least one of the distal femur and the proximal tibia, the graphical representations including:
  medial total gap;
  medial recommended resection;
  lateral total gap;
  lateral recommended resection; and
  at least a portion of a recommended implant to replace a portion of the distal femur or the proximal tibia; and
  outputting the graphical user interface to the display device,
  wherein generating the graphical user interface includes generation of a medial overlap indicator and a lateral overlap indicator overlaid onto the graphical representation of the distal femur and the proximal tibia within the interactive trapezoidal graphic.

* * * * *

UNITED STATES PATENT AND TRADEMARK OFFICE
CERTIFICATE OF CORRECTION

PATENT NO. : 11,229,489 B2
APPLICATION NO. : 15/853657
DATED : January 25, 2022
INVENTOR(S) : Merette et al.

Page 1 of 1

It is certified that error appears in the above-identified patent and that said Letters Patent is hereby corrected as shown below:

On the Title Page

In item (72), in "Inventors", in Column 1, Line 8, delete "Motreal" and insert --Montreal-- therefor On page 3, in Column 1, under "Other Publications", Line 23, delete "dated dated" and insert --dated-- therefor In the Claims In Column 24, Line 22, in Claim 18, delete "Ari" and insert --An-- therefor Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*